(12) United States Patent
Chen et al.

(10) Patent No.: US 12,290,073 B2
(45) Date of Patent: May 6, 2025

(54) ANTI-MICROBIAL COMPOUND AND METHODS OF USE

(71) Applicant: SHENZHEN UNIVERSITY, Guangdong (CN)

(72) Inventors: Shiguo Chen, Shenzhen (CN); Jingwei Gu, Shenzhen (CN)

(73) Assignee: SHENZHEN UNIVERSITY, Shenzhen (CN)

( * ) Notice: Subject to any disclaimer, the term of this patent is extended or adjusted under 35 U.S.C. 154(b) by 824 days.

(21) Appl. No.: 17/447,446

(22) Filed: Sep. 13, 2021

(65) Prior Publication Data

US 2022/0030870 A1 Feb. 3, 2022

Related U.S. Application Data

(63) Continuation of application No. PCT/CN2020/078468, filed on Mar. 9, 2020.

(30) Foreign Application Priority Data

Mar. 11, 2019 (CN) .......................... 201910181723.9

(51) Int. Cl.
*A01N 43/66* (2006.01)
*D06M 16/00* (2006.01)

(52) U.S. Cl.
CPC ............. *A01N 43/66* (2013.01); *D06M 16/00* (2013.01)

(58) Field of Classification Search
CPC .................................................... A01N 43/66
USPC ........................................................ 544/180
See application file for complete search history.

(56) References Cited

U.S. PATENT DOCUMENTS 3,074,814 A * 1/1963 Sause ................. D06M 13/358
544/194

FOREIGN PATENT DOCUMENTS

| CN | 101081873 A | 12/2007 |
|---|---|---|
| CN | 101760962 A | 6/2010 |
| CN | 102715170 A | 10/2012 |
| CN | 103881081 A | 6/2014 |
| CN | 106632259 A | 5/2017 |
| CN | 106928158 A | 7/2017 |
| CN | 109912991 A | 6/2019 |
| EP | 0556216 B1 | 6/1997 |
| JP | S4969678 A | 7/1974 |
| RU | 2466728 C1 | 11/2012 |
| WO | 2020182100 A1 | 9/2020 |

OTHER PUBLICATIONS

The Third Office Action in Chinese Application No. 201910181723.9 mailed on Apr. 6, 2022, 16 pages.
He, Liang et al., Constructing Safe and Durable Antibacterial Textile Surfaces Using a Robust Graft-to Strategy Via Covalent Bond Formation, Scientific Reports, 36327(6): 1-9, 2016.
International Search Report in PCT/CN2020/078468 mailed on Jun. 2, 2020, 5 pages.
Written Opinion in PCT/CN2020/078468 mailed on Jun. 2, 2020, 5 pages.
First Office Action in Chinese Application No. 201910181723.9 mailed on May 8, 2021, 17 pages.
Han, Lijuan et al., Ecological Staining Technique and Health Function Research of Silk with Tea-leaves, Textile Technology Progress, 2010, 5 pages.

* cited by examiner

*Primary Examiner* — Taofiq A Solola
(74) *Attorney, Agent, or Firm* — METIS IP LLC

(57) ABSTRACT

The present disclosure provides a compound and methods of preparing the compound. The compound has anti-microbial and anti-mite properties and can be bonded to materials such as fiber and synthetic polymer. The compound may also be used in a finishing agent for textiles, fibers, or yarns to protect these materials against microorganisms and mites. Additionally, when these materials are treated with a relatively low dosage of the compound, long-lasting and effective anti-mold and anti-mite effects may be achieved at a relatively low cost.

10 Claims, 7 Drawing Sheets

ANTI-MICROBIAL COMPOUND AND METHODS OF USE

CROSS-REFERENCE TO RELATED APPLICATIONS

This application is a continuation of International Application No. PCT/CN2020/078468, filed on Mar. 9, 2020, which claims priority to Chinese Application No. 201910181723.9, filed on Mar. 11, 2019, the entire contents of each of which are hereby incorporated by reference.

TECHNICAL FIELD

The present disclosure generally relates to anti-microbial compounds and methods of using the anti-microbial compounds for killing microorganisms and/or mites.

BACKGROUND

Natural fibers (e.g., cotton, hemp, silk, wool, etc.) are one of the most commonly-used textile materials. The cotton textile industry plays an important role in the development of economy. Cotton textiles are popular for their properties such as softness, breathability, moisture absorption and comfortable wearing. However, some pathogenic microorganisms (e.g., bacteria and/or mites) are capable of growing rapidly on the surface of cotton textiles, forming plaques or microbial membranes, causing disease or infection, which may significantly affect the usability and aesthetics of cotton textiles. Therefore, it would be desirable to improve the anti-microbial properties of natural fibers such as cotton textile, thus improving their safety and popularity.

Surface modification of natural fibers may be achieved by changing the structure of the compound on its surface. At present, one of the most commonly used processing technologies for textile modification is a finishing process. The finishing process is relatively simple and scalable for production. It involves a functional treatment of shaped textiles, generally by coating or immersing the textiles using a finishing agent. Thus, an anti-microbial agent may be absorbed by or chemically bonded to the surface of the natural fiber to obtain a certain degree of anti-microbial performance.

The anti-microbial nature of anti-microbial agents and their ability to bind to fibers is a key factor in determining their wide availability. Therefore, it is desired to provide compounds capable of killing microorganisms and such compounds can be used to improve the anti-microbial properties of materials such as textiles.

SUMMARY

According to an aspect of the present disclosure, a compound is provided. The compound may have a structure represented by a general formula (I):

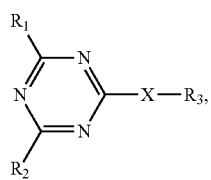
(I)

where $R_1$ may be halogen, preferably Br, Cl or I; $R_2$ may be H, halogen, $-NO_2$ or $C_{1-8}$ hydrocarbyl that may be unsubstituted or substituted with one or more heteroatoms; X may be NH, O, S or $C_{1-18}$ hydrocarbyl that may be unsubstituted or substituted with one or more heteroatoms; and $R_3$ may include at least one of a quaternary ammonium salt group or a quaternary phosphonium salt group.

In some embodiments, $R_3$ may be

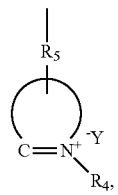

where Y may be halogen, preferably Br, Cl or I; $R_4$ may be $C_{1-18}$ hydrocarbyl that may be unsubstituted or substituted with one or more heteroatoms, preferably $C_{1-18}$ alkyl; and $R_5$ may be $C_{0-18}$ hydrocarbyl that may be unsubstituted or substituted with one or more heteroatoms, preferably $C_{1-18}$ alkyl.

In some embodiments, $R_3$ may be

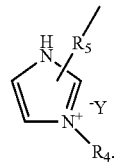

In some embodiments, $R_3$ may be

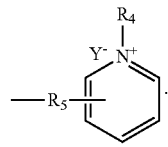

In some embodiments, $R_3$ may be

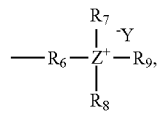

where: Z may be N or P; Y may be halogen, preferably Br, Cl or I; $R_6$ may be $C_{1-18}$ hydrocarbyl that may be unsubstituted or substituted with one or more heteroatoms, preferably $C_{1-18}$ alkyl; $R_7$ may be $C_{1-18}$ hydrocarbyl that may be unsubstituted or substituted with one or more heteroatoms, preferably $C_{1-18}$ alkyl, phenyl or substituted phenyl; $R_8$ may be $C_{1-18}$ hydrocarbyl that may be unsubstituted or substituted with one or more heteroatoms, preferably $C_{1-18}$ alkyl, phenyl or substituted phenyl; and $R_9$ may be $C_{1-18}$ hydrocarbyl that may be unsubstituted or substituted with one or more heteroatoms, preferably $C_{1-18}$ alkyl, phenyl or substituted phenyl.

In some embodiments, $R_7$ and $R_8$ may be the same or different.

In some embodiments, the structural formula of the compound may be

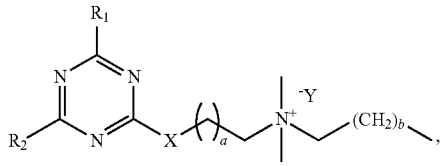

where a=0-17, preferably 0, 1, 3, 5, 7, 9, 11, 13, 15 or 17; b=0-17, preferably 0, 1, 3, 5, 7, 9, 11, 13, 15 or 17; and X=O, S, NH or —$(CH_2)_n$—, n=1-18.

In some embodiments, $R_3$ may be

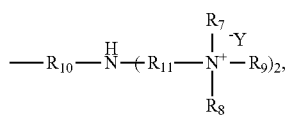

where $R_{10}$ may be $C_{1-18}$ hydrocarbyl that may be unsubstituted or substituted with one or more heteroatoms, preferably $C_{1-18}$ alkyl; and $R_{11}$ may be $C_{1-18}$ hydrocarbyl that may be unsubstituted or substituted with one or more heteroatoms, preferably $C_{1-18}$ alkyl.

In some embodiments, X may be NH.

In some embodiments, $R_3$ may be

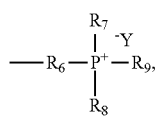

where $R_7$ may be phenyl, substituted phenyl or —$(CH_2)_{n1}$—, where n1 may be a positive integer, preferably 1, 2, 3 or 6-18; $R_8$ may be phenyl, substituted phenyl or —$(CH_2)_{n2}$—, where n2 may be a positive integer, preferably 1, 2, 3 or 6-18; and $R_9$ may be phenyl, substituted phenyl or —$(CH_2)_{n3}$—, where n3 may be a positive integer, preferably 1, 2, 3 or 6-18.

In some embodiments, $R_7$, $R_8$, and $R_9$ may be the same or different.

According to another aspect of the present disclosure, a compound is provided. The compound may have a structure of a general formula (II):

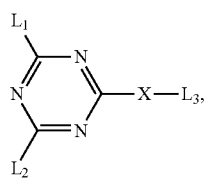

(II)

where: $L_1$ may be halogen; $L_2$ may be selected from the group consisting of H, halogen, $NO_2$, $C_{1-18}$ hydrocarbyl that may be substituted with one or more heteroatoms or may be unsubstituted; X may be selected from the group consisting of NH, O, S; and $L_3$ may include at least one of a quaternary ammonium salt group or a quaternary phosphonium salt group.

In some embodiments, $L_3$ may be

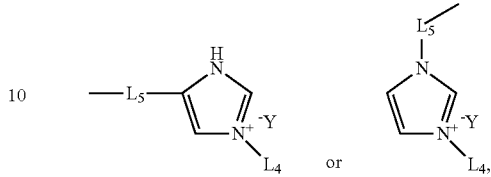

where: Y may be selected from the group consisting of Cl, Br, I; $L_4$ may be $C_dH_m$, where d=1-18, m=1-37; $L_5$ may be $C_nH_q$, where n=1-18, q=1-17.

In some embodiments, d may be 1, 8, 14 or 18, and a may be 2, 3 or 18.

In some embodiments, X may be NH or O, and Y may be Br.

In some embodiments, $L_3$ may be

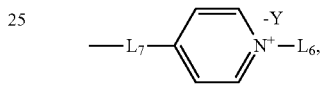

where Y may be selected from the group consisting of Cl, Br, I; $L_6$ may be a $C_{1-18}$ hydrocarbyl that may be substituted with one or more heteroatoms or may be unsubstituted; and $L_7$ may be a $C_{1-18}$ hydrocarbyl that may be substituted with one or more heteroatoms or may be unsubstituted.

In some embodiments, $L_6$ and $L_7$ may be alkyl groups.

In some embodiments, $L_6$ may be —$CH_3$ or —$(CH_2)_9$—$CH_3$, and $L_7$ may be —$CH_3$ or —$CH_2CH_3$.

In some embodiments, $L_3$ may be

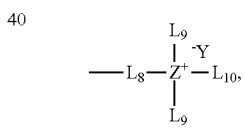

where: Z may be N or P; Y may be halogen; $L_8$ may be a $C_{1-18}$ hydrocarbyl that may be substituted with one or more heteroatoms or may be unsubstituted; $L_9$ may be $C_{1-18}$ hydrocarbyl that may be substituted with one or more heteroatoms or may be unsubstituted; and $L_{10}$ may be $C_{1-18}$ hydrocarbyl that may be substituted with one or more heteroatoms or may be unsubstituted.

In some embodiments, $L_8$ may be —$(CH_2)_u$—, where u=0-18; $L_9$ may be —$CH_3$ or phenyl that may be unsubstituted or substituted with one or more heteroatoms; and $L_{10}$ may be —$(CH_2)_v$—$CH_3$, where v=0-17.

In some embodiments, $L_3$ may be

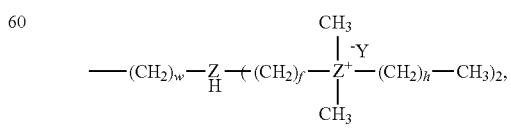

where: Y may be halogen; Z may be N or P; w=0-18; f=0-18; and h=0-17.

In some embodiments, w=2; f=1, 2 or 18; and h=0, 9 or 11.

In some embodiments, X may be O.

In some embodiments, $L_3$ is

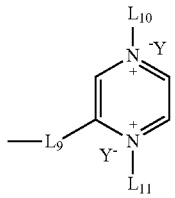

where: Y may be halogen; $L_9$ may be a $C_{1-18}$ hydrocarbyl that may be substituted with one or more heteroatoms or may be unsubstituted; $L_{10}$ may be a $C_{1-18}$ hydrocarbyl that may be substituted with one or more heteroatoms or may be unsubstituted; and $L_{11}$ may be a $C_{1-18}$ hydrocarbyl that may be substituted with one or more heteroatoms or may be unsubstituted.

In some embodiments, $L_{10}$ may be —(CH$_2$)$_i$—CH$_3$, where i may be 0-17; and $L_{11}$ may be —(CH$_2$)$_j$—CH$_3$, where j may be 0-17.

In some embodiments, $L_{10}$ and $L_{11}$ may be the same.

In some embodiments, $L_1$ may be Cl.

According to yet another aspect of the present disclosure, a method of preparing a compound is provided. The method may include reacting HX—R$_3$ with a compound having a structure represented by the general formula (III) to obtain the compound (I);

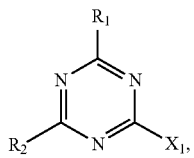

(III)

where $X_1$ may be halogen, preferably Br, Cl or I.

In some embodiments, the reacting HX—R$_3$ with a compound having a structure represented by the general formula (III) to obtain the compound (I) may include reacting HX—R$_3$ with the compound having the structure represented by the general formula (III) under the presence of a Lewis base. The Lewis base may be preferably selected from the group consisting of alkali metal, inorganic base of alkaline earth metal, and an organic tertiary amine.

In some embodiments, the inorganic base may be selected from the group consisting of sodium hydroxide, potassium hydroxide, magnesium hydroxide, calcium hydroxide, potassium carbonate, potassium hydrogencarbonate, sodium carbonate, sodium hydrogencarbonate, and combinations thereof; and the organic tertiary amine may be selected from the group consisting of N, N-diisopropyl-ethylamine, trimethylamine, triethylamine, N, N-dimethyl-n-octylamine, N, N-dimethylaniline, N, N-dimethyl-dodecylamine, N, N-dimethyl-dodecylamine, N, N-dimethyl-hexadecylamine, N, N-dimethyl-octadecylamine, N, N-dimethyl-decylamine, dimethylaminoethyl methacrylate, diethylaminoethyl methacrylate, and combinations thereof.

According to still another aspect of the present disclosure, a method of preparing the compound is provided. The method may include producing HX—R$_3$ by reacting

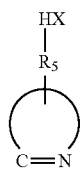

with Y—R$_4$; reacting HX—R$_3$ with a compound having a structure represented by the general formula (III) to obtain the compound (I);

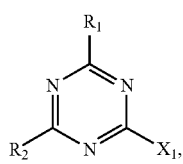

(III)

where $X_1$ may be halogen, preferably Br, Cl or I.

According to still another aspect of the present disclosure, a method of preparing the compound is provided. The method may include producing HX—R$_3$ by reacting

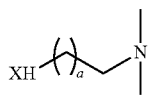

with Y—(CH$_2$)$_b$CH$_3$; and reacting HX—R$_3$ with a compound having a structure represented by the general formula (III) to obtain the compound (I);

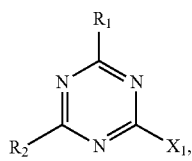

(III)

where $X_1$ may be halogen, preferably Br, Cl or I.

According to yet another aspect of the present disclosure, a method of preparing the compound is provided. The method may include producing

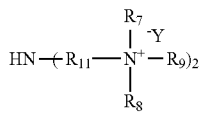

by reacting

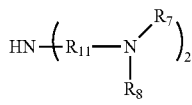

with Y—R$_9$; producing HX—R$_3$ by reacting

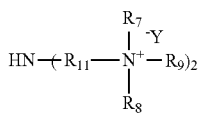

with HX—R$_{10}$-Q, Q being halogen, preferably Br, Cl or I; and reacting HX—R$_3$ with a compound having a structure represented by the general formula (III) to obtain the compound (I);

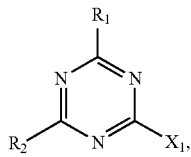

(III)

where X$_1$ may be halogen, preferably Br, Cl or I.

According to still another aspect of the present disclosure, a method of preparing the compound is provided. The method may include producing HX—R$_3$ by reacting

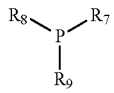

with Y—R$_6$—HX; and reacting HX—R$_3$ with a compound having a structure represented by the general formula (III) to obtain the compound (I);

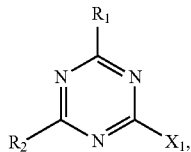

(III)

where X$_1$ may be halogen, preferably Br, Cl or I.

In some embodiments, R$_1$ may be Cl.

According to yet another aspect of the present disclosure, an anti-microbial or anti-mite product is provided. The product may include the compound.

In some embodiments, the product may further include one or more auxiliary components.

In some embodiments, the one or more auxiliary components may be selected from the group consisting of cosolvents, pH adjusting agents, hydrophobicizers, oleophobicizers, binders, crosslinks, surfactants, softeners, dyes, flame retardants, textile dyes, sewability improvers, and combinations thereof.

In some embodiments, the pH adjusting agents may include Lewis base, preferably at least one of sodium carbonate, sodium hydrogencarbonate, potassium carbonate, potassium hydrogencarbonate, triethylamine, trimethylamine or tributylamine.

In some embodiments, the surfactants may include at least one of stearic acid, sodium dodecylbenzene sulfonate, sodium hexadecyl sulfonate, sodium stearyl sulfonate, sodium cetyl carboxylate, sodium lauryl sulfate, sodium hexadecyl sulfate, sodium lauryl carboxylate, lecithin or fatty acid glycerides.

In some embodiments, the product may include a solvent selected from the group consisting of water, dimethyl sulfoxide, chloroform, ether, ketone, ester, nitrile, amide, aromatic compound, and combinations thereof.

In some embodiments, the ether may be selected from the group consisting of tetrahydrofuran, 1, 4-dioxane, ethylene glycol dimethyl ether, and combinations thereof. The ketone may be selected from the group consisting of acetone, methyl ethyl ketone, cyclohexanone, acetophenone, phorone, and combinations thereof. The aromatic compound may be selected from the group consisting of toluene, pyridine, imidazole, and combinations thereof.

In some embodiments, the ester may be selected from the group consisting of ethyl acetate, n-butyl acetate, n-propyl acetate, ethyl formate, methyl formate, and combinations thereof. The nitrile may be selected from the group consisting of acetonitrile, propionitrile, benzonitrile, and combinations thereof; and the amide may be selected from the group consisting of N, N-dimethyl-acetamide, N, N-dimethyl-formamide and N, N-dimethyl-pyrrolidone.

In some embodiments, the cosolvent may be selected from the group consisting of water, dimethyl sulfoxide, ether, ketone, ester, nitrile, amide aromatic compound, and combinations thereof.

In some embodiments, the ether in the cosolvent may be selected from the group consisting of tetrahydrofuran, 1, 4-dioxane, ethylene glycol dimethyl ether, and combinations thereof. The ketone in the cosolvent may be selected from the group consisting of acetone, methyl ethyl ketone, cyclohexanone, acetophenone, phorone, and combinations thereof. The aromatic compound in the cosolvent may be selected from the group consisting of toluene, pyridine, imidazole, and combinations thereof.

In some embodiments, the ester in the cosolvent may be selected from the group consisting of ethyl acetate, n-butyl acetate, n-propyl acetate, ethyl formate, methyl formate, and combinations thereof. The nitrile in the cosolvent may be selected from the group consisting of acetonitrile, propionitrile, benzonitrile, and combinations thereof. The amide in the cosolvent may be selected from the group consisting of N, N-dimethylacetamide, N, N-dimethylformamide, N, N-dimethylpyrrolidone, and combinations thereof.

In some embodiments, the content of cosolvent may be 0-12% of the product by weight, preferably 0.1-10%.

In some embodiments, the content of surfactants may be 0.01-2% of the product by weight, preferably 0.05%-0.08%.

In some embodiments, the content of the compound may be 0.05%-10% of the product by weight.

In some embodiments, the content of the compound may be 0.1-5% of the product by weight.

In some embodiments, the pH of the product may be between 8-11.

In some embodiments, the pH of the product may be 8, 8.5, 9, 9.5, 10, 10.5, or 11.

In some embodiments, the product may be used to kill microorganisms or mites.

In some embodiments, the microorganisms include at least one of *Escherichia coli, Staphylococcus aureus, Candida albicans*, or *Aspergillus niger*.

In some embodiments, the product may be a finishing agent for treating textiles, fibers, or yarns.

In some embodiments, the product further includes a solid support. The compound may be used to improve anti-microbial or anti-mite abilities of the solid support. The solid support may be selected from the group consisting of wood, synthetic polymers, fibers, cloth, paper, rubber, glass, or metal.

In some embodiments, the compound may be chemically bonded to the solid support.

According to still another aspect of the present disclosure, a use of the compound for killing microorganisms or mites is provided.

In some embodiments, the microorganisms include at least one of *Escherichia coli, Staphylococcus aureus, Candida albicans*, or *Aspergillus niger*.

In some embodiments, the mites include at least one of dust mites, fur mites, or parasitic mites.

According to yet another aspect of the present disclosure, a method for killing microorganisms or mites in a target object is provided. The target object may include applying the product to the target object by using the product to contact the target object.

In some embodiments, the microorganisms include at least one of *Escherichia coli, Staphylococcus aureus, Candida albicans*, or *Aspergillus niger*.

In some embodiments, the mites may be selected from the group consisting of dust mites, fur mites, or parasitic mites.

In some embodiments, the target object may include at least one of wood, synthetic polymers, fibers, cloth, paper, rubber, glass, or metal.

In some embodiments, the target object may be selected from the group consisting of textiles, fibers, yarns, food packaging materials, medical devices, and combinations thereof.

In some embodiments, the using the product to contact the target object may include at least one of a soaking process, a padding process, a spraying process, or a brushing-coating process.

In some embodiments, the using the product to contact the target object includes: soaking the target object in the product for a predetermined time period, where the product may be diluted or undiluted, and the predetermined time period may be between 1 second (s) to 60 minutes (min).

In some embodiments, the predetermined time period may be 1 s, 5 s, 10 s, 20 s, 30 s, 60 s, 5 min, 10 min, 15 min, 20 min, 30 min or 60 min.

In some embodiments, the method may further include heating the target object at the temperature of 60-150° C.

In some embodiments, the temperature may be 80° C., 85° C., 90° C., 95° C., 100° C., or 105° C.

In some embodiments, the weight of the product may be 5-50 times of the weight of the target object.

In some embodiments, the weight of the product may be 10, 15, 20, 25 or 30 times of the weight of the target object.

According to still another aspect of the present disclosure, a target object treated by the method of any one of claims is provided.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. It should be noted that the drawings are not to scale. These embodiments are non-limiting exemplary embodiments, in which like reference numerals represent similar structures throughout the several views of the drawings, and wherein.

DETAILED DESCRIPTION

Figure 1:
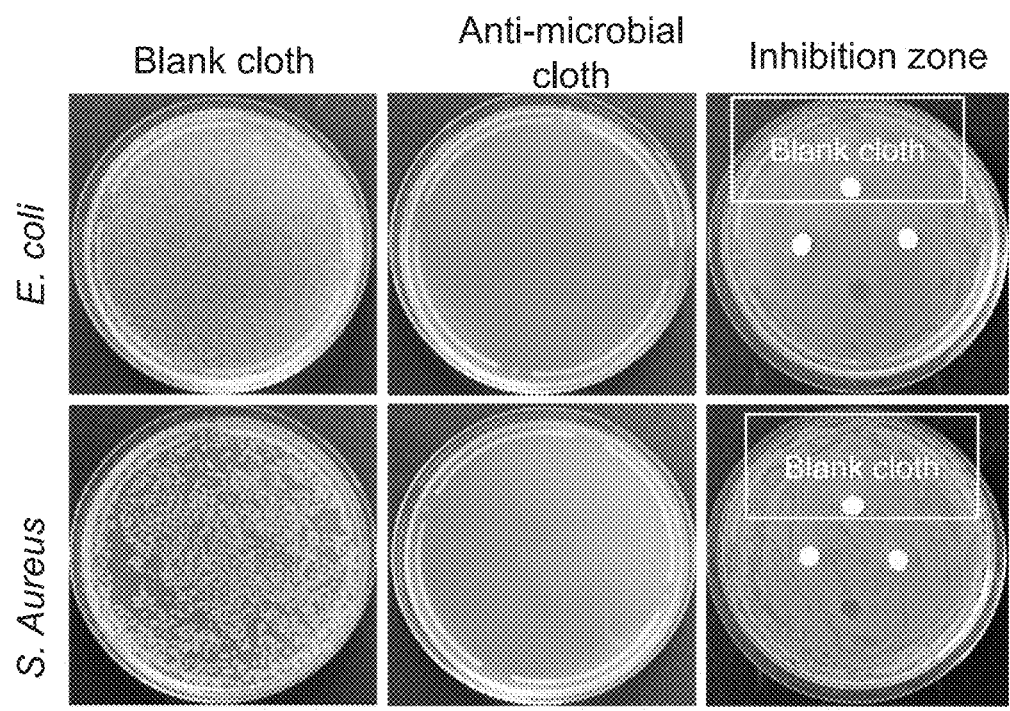
FIG. 1 is a group of images showing the anti-microbial effects when textiles are treated with compound E obtained in Example 2, comparing to un-treated textiles according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing (s), all of which form a part of this specification. It is to be expressly understood, however, that the drawing (s) are for the purpose of illustration and description only and are not intended to limit the scope of the present disclosure. It is understood that the drawings are not to scale.

An aspect of the present disclosure provides a compound. The compound has anti-microbial and anti-mite properties and can be chemically bonded to materials such as fiber and synthetic polymer. The compound has no significant negative influence on the mechanical properties of the materials. The compound may also be used in a finishing agent for textiles, fibers, or yarns to protect these materials against microorganisms and mites. Additionally, when these materials are treated with a relatively low dosage of the compound, long-lasting and effective anti-mold and anti-mite effects may be achieved at a relatively low cost. The compound may further improve the softness and antistatic properties of the textiles. In the following descriptions, the structure of the compound is described.

In some embodiments, the compound has the structure of a general formula (I):

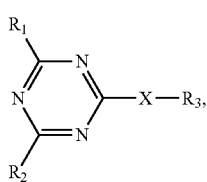

(I)

where $R_1$ is halogen, such as Cl, Br or I; $R_2$ is halogen (such as Cl, Br or I), hydrogen, or $C_{1-8}$ hydrocarbyl that is unsubstituted or substituted with one or more heteroatoms; X is NH, O, S or $C_{1-18}$ hydrocarbyl that is unsubstituted or substituted with one or more heteroatoms; $R_3$ contains at least one of a quaternary ammonium salt group or a quaternary phosphonium salt group.

When $R_2$ is selected from unsubstituted or substituted $C_{1-8}$ alkyl groups, $R_2$ may be a linear alkyl group or a branched alkyl group, and may be unsubstituted or substituted by one or more heteroatoms, such as a $C_{1-8}$ straight or branched alkyl group. For example, methyl, ethyl, propyl or isopropyl, or the like, or substituted by one or more heteroatoms (such as N, P, S, O, etc.).

When $R_2$ is selected from unsubstituted or substituted $C_{1-8}$ cycloalkyl groups, $R_2$ may be selected from a cyclopropyl group, a substituted cyclopropyl group, a cyclobutyl group, a substituted cyclobutyl group, a cyclopentyl group, a substituted cyclopentyl group, a cyclohexyl group, and a substituted cyclohexyl group.

When $R_2$ is selected from unsubstituted or substituted $C_{1-8}$ olefin groups, it may be selected from $CH_2=CH-(CH_2)_n-$, where n=1-6, such as 1, 2, 3, 4, 5 or 6, and a substituted $CH_2=CH-(CH_2)_n-$ group in which hydrogen is substituted.

When $R_2$ is selected from unsubstituted or substituted aromatic hydrocarbyl, it may be selected from substituted or unsubstituted $C_6H_5CH=CH-$, $C_6H_5CH=CH-CH_2-$, $C_6H_5-CH_2CH=CH-CH_2-$, or an aromatic group containing one or more heteroatoms such as pyridine, furan or thiophene.

The compound may have the following characteristics:
(1) the halogen-substituted triazine compound can react with the —OH and —$NH_2$ groups on the surface of materials such as fiber/synthetic polymer via a nucleophilic substitution reaction, thereby firmly binding to the materials and being resistant to washing.
(2) $R_3$ contains at least one of a quaternary ammonium salt group or a quaternary phosphonium salt group. The quaternary ammonium salt group and the quaternary phosphonium salt group have good bactericidal effects and have higher anti-microbial, anti-mold and anti-mite activities than zwitterionic bacteriostatic agents (the key component is zwitterions). Products (e.g., textiles) with long-lasting and highly efficient mold-proof and smash-proof properties can be obtained by using a relatively low dosage of the compound, while also improving the softness and antistatic properties of the textiles.

In some embodiments, compounds with the structure of the general formula (I) may be used for anti-microbial finishing of textiles, and the textiles may have significant anti-microbial properties. Thus, they can be used as/in an anti-microbial agent, or used for the preparation of the anti-microbial agent for achieving long-lasting anti-microbial effects of materials in fields such as textile, medicine, and food packaging, but the use of the compound is not limited to these fields.

In some embodiments, the compound provided by the present disclosure may have the following properties: textiles with broad-spectrum, long-lasting, and highly effective anti-microbial/anti-mite properties may be obtained at a relatively low cost since a low dosage of the compound is needed. The compound may further improve the softness and antistatic properties of the textiles. Under the premise that the mechanical properties, moisture permeability, and color of the textiles are not negatively affected by the compound, the textiles may have relatively good anti-microbial, anti-mold, and/or anti-mite effects, a relatively strong bonding ability with fibers, better anti-microbial durability against washing, a relatively low cost, a convenient use, a simple finishing process, no waste gas discharge, a potential for automization, or the like, or any combination thereof. As used herein, the potential for automization refers to that the compound may be used in an automatic process for improving the antimicrobial and/or anti-mite properties of materials since the operations in the finishing process are relatively simple to operate.

In some embodiments of the present disclosure, $R_3$ is

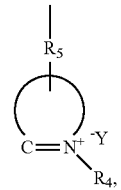

Y is halogen, preferably Br, Cl or I; $R_4$ is $C_{1-18}$ hydrocarbyl that is unsubstituted or substituted with one or more heteroatoms, preferably $C_{1-18}$ alkyl, which may be a linear alkyl group or a branched alkyl group, which may be unsubstituted or substituted by one or more heteroatoms, such as a $C_{1-18}$ linear or branched alkyl group, for example, methyl, ethyl, propyl or isopropyl, or the like, or the fore-mentioned groups that are substituted by one or more heteroatoms (such as N, P, S, O, etc.);

$R_5$ is a $C_{0-18}$ hydrocarbyl that is unsubstituted or substituted with one or more heteroatoms, preferably $C_{1-18}$ alkyl which may be a linear alkyl group or a branched alkyl group, which may be unsubstituted or substituted by one or more heteroatoms, such as a $C_{1-18}$ linear or branched alkyl group, for example, methyl, ethyl, propyl or isopropyl, or the like, or the fore-mentioned groups that are substituted by one or more heteroatoms (such as N, P, S, O, etc.).

The quaternary ammonium salt ring in

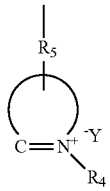

may be a three-membered ring, a four-membered ring, a five-membered ring, a six-membered ring, a seven-membered ring, or the like, which is not limited to a pyrrole ring, a pyrazole ring, an imidazole ring, an indazole ring, a pyridazine ring, a pyrimidine ring, a pyrazine ring, or a fused heterocyclic ring containing the above groups.

When $R_5$ is $C_0$, it means that

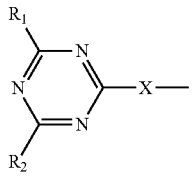

is directly connected to the ring of

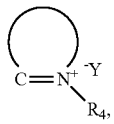

that is, the general formula of the compound (I) is:

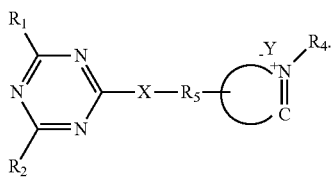

In some embodiments of the present disclosure, $R_3$ is

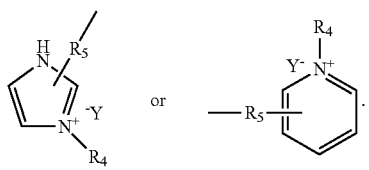

In some embodiments of the present disclosure, $R_3$ is

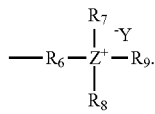

Z is N or P.

$R_6$ is $C_{1-18}$ hydrocarbyl that is unsubstituted or substituted with one or more heteroatoms, preferably $C_{1-18}$ alkyl. For example, $R_6$ may be $—(CH_2)_n—$, where n=1-18 (e.g., 1, 2, 3, 4, 5, 6, 7, 8, 9, 10, 11, 12, 13, 14, 15, 16, 17 or 18). Alternatively, $R_6$ may be an isomer of $—(CH_2)_n—$;

$R_7$ is $C_{1-18}$ hydrocarbyl that is unsubstituted or substituted with one or more heteroatoms, preferably $C_{1-18}$ alkyl, phenyl or substituted phenyl; $C_{1-18}$ alkyl may be, for example, $—(CH_2)_{n1}—$, where n1=1-18 (e.g., 1, 2, 3, 4, 5, 6, 7, 8, 9, 10, 11, 12, 13, 14, 15, 16, 17, or 18), or may be an isomer of $—(CH_2)_{n1}—$;

$R_8$ is $C_{1-18}$ hydrocarbyl that is unsubstituted or substituted with one or more heteroatoms, preferably $C_{1-18}$ alkyl, phenyl or substituted phenyl; $C_{1-18}$ alkyl such as $—(CH_2)_{n2}—$, n2=1-18 (e.g., 1, 2, 3, 4, 5, 6, 7, 8, 9, 10, 11, 12, 13, 14, 15, 16, 17, or 18), or an isomer of $—(CH_2)_n—$;

$R_9$ is a heteroatom substituted or unsubstituted C1-18 hydrocarbyl, preferably a C1-18 alkyl group, a benzene ring or a substituted benzene ring; C1-18 alkyl such as $—(CH_2)_{n3}—$, n3=1-18 (e.g., 1, 2, 3, 4, 5, 6, 7, 8, 9, 10, 11, 12, 13, 14, 15, 16, 17, or 18), or an isomer of $—(CH_2)_n—$.

In some embodiments, $R_7$ and $R_8$ are the same or different groups. For example, $R_7$ and $R_8$ may be methyl, ethyl, isopropyl, n-butyl, n-pentyl or cyclohexyl.

In some embodiments of the present disclosure, the structural formula (I) of Compound is:

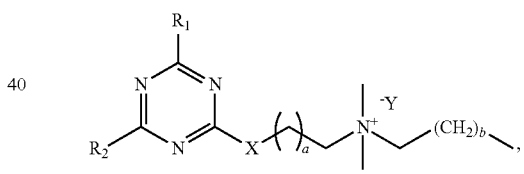

where a=0 to 17 (for example, 0, 1, 2, 3, 4, 5, 6, 7, 8, 9, 10, 11, 12, 13, 14, 15, 16 or 17), and b=0 to 17 (for example, 0, 1, 2, 3, 4, 5, 6, 7, 8, 9, 10, 11, 12, 13, 14, 15, 16 or 17).

In some embodiments of the present disclosure, $R_3$ is

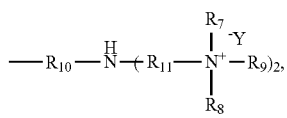

where $R_6$ is $C_{1-18}$ hydrocarbyl that is unsubstituted or substituted with one or more heteroatoms, preferably $C_{1-18}$ alkyl. For example, $R_6$ may be $—(CH_2)_n—$, where n=1-18 (e.g., 1, 2, 3, 4, 5, 6, 7, 8, 9, 10, 11, 12, 13, 14, 15, 16, 17 or 18), or $R_6$ may be an isomer of $—(CH_2)_n—$.

$R_7$ is $C_{1-18}$ hydrocarbyl that is unsubstituted or substituted with one or more heteroatoms, preferably $C_{1-18}$ alkyl, phenyl or substituted phenyl; $C_{1-18}$ alkyl may be, for example, $—(CH_2)_{n1}—$, where n1=1-18 (e.g., 1, 2, 3, 4, 5, 6, 7, 8, 9, 10, 11, 12, 13, 14, 15, 16, 17, or 18), or may be an isomer of $—(CH_2)_n—$.

R₉ is C₁₋₁₈ hydrocarbyl that is unsubstituted or substituted with one or more heteroatoms, preferably C₁₋₁₈ alkyl, phenyl or substituted phenyl; C₁₋₁₈ alkyl may be, for example, —(CH₂)ₙ₃—, where n3=1-18 (e.g., 1, 2, 3, 4, 5, 6, 7, 8, 9, 10, 11, 12, 13, 14, 15, 16, 17, or 18), or may be an isomer of —(CH₂)ₙ—.

R₁₀ is C₁₋₁₈ hydrocarbyl that is unsubstituted or substituted with one or more heteroatoms, preferably C₁₋₁₈ alkyl, phenyl or substituted phenyl; C₁₋₁₈ alkyl may be, for example, —(CH₂)ₙ—, where n=1-18 (e.g., 1, 2, 3, 4, 5, 6, 7, 8, 9, 10, 11, 12, 13, 14, 15, 16, 17, or 18), or may be an isomer of —(CH₂)ₙ—;

R₁₁ is C₁₋₁₈ hydrocarbyl that is unsubstituted or substituted with one or more heteroatoms, preferably C₁₋₁₈ alkyl, phenyl or substituted phenyl; C₁₋₁₈ alkyl may be, for example, —(CH₂)ₙ—, where n=1-18 (e.g., 1, 2, 3, 4, 5, 6, 7, 8, 9, 10, 11, 12, 13, 14, 15, 16, 17, or 18), or may be an isomer of —(CH₂)ₙ—.

In some embodiments of the present disclosure, R₇, R₈, and R₉ are the same group, or different groups.

In some embodiments of the present disclosure, R₃ is

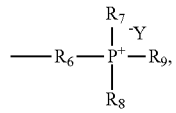

R₆ is —(CH₂)ₙ—, and n is a positive integer, preferably 1-18. More preferably 2 to 18, such as 2, 3, 4, 5, 6, 7, 8, 9, 10, 11, 12, 13, 14, 15, 16, 17, or 18;

R₇ is a benzene ring, a substituted benzene ring, or —(CH₂)ₙ₁—, n1 is a positive integer, preferably 1, 2, 3 or 6-18;

R₈ is a benzene ring or a substituted benzene ring, —(CH₂)ₙ₂—, n2 is a positive integer, preferably 1, 2, 3 or 6-18;

R₉ is a benzene ring or a substituted benzene ring, —(CH₂)ₙ₃—, n3 is a positive integer, preferably 1, 2, 3 or 6-18.

In some embodiments, the bridging bond X between the triazine ring and the quaternary ammonium salt is preferably NH, O or S.

In some embodiments of the present disclosure, R₇, R₈, and R₉ are the same group, or are different groups.

In some embodiments of the present disclosure, the compound (I) is one of the following:

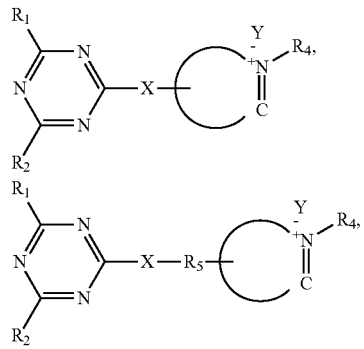

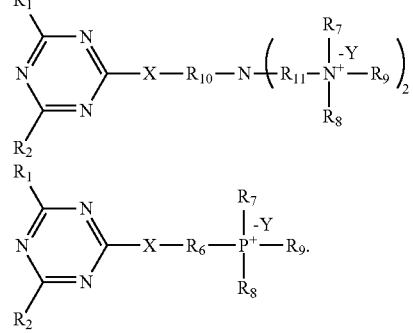

In some embodiments, the compound having the formula

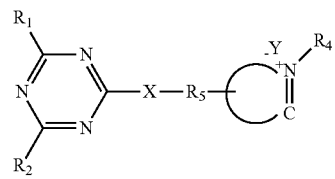

may include at least one of the following:

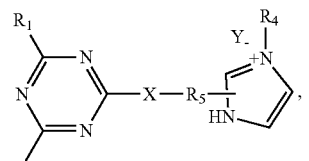

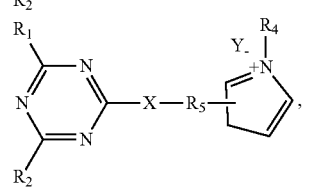

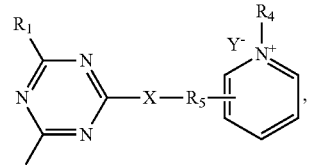

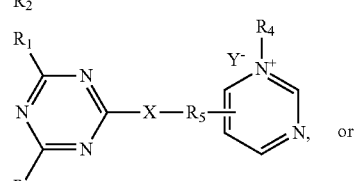

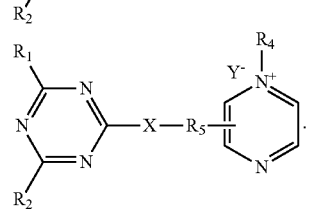

In some embodiments, the structure of the compound may be described using a general formula (II):

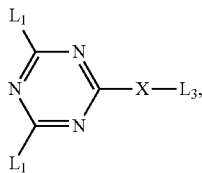

(II)

where: $L_1$ is halogen, such as Cl, Br or I; $L_2$ is selected from the group consisting of H, halogen, $NO_2$, $C_{1-18}$ hydrocarbyl that is substituted with one or more heteroatoms or is unsubstituted; X is selected from the group consisting of NH, O, S; and $L_3$ may include at least one of a quaternary ammonium salt group or a quaternary phosphonium salt group.

In some embodiments, $L_3$ is

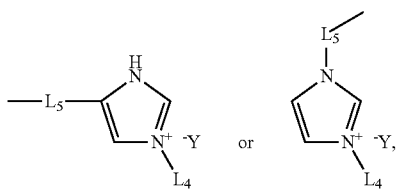

where Y is selected from the group consisting of Cl, Br, I; $L_4$ is $C_dH_m$, where d=1-18, m=1-37; $L_5$ is $C_nH_q$, where n=1-18, q=1-17.

In some embodiments, d is 1, 8, 14 or 18, and a is 2, 3 or 18.

In some embodiments, X is NH or O, and Y is Br.

In some embodiments, $L_3$ is

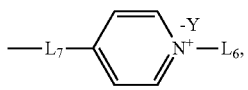

where Y is selected from the group consisting of Cl, Br, I; $L_6$ is $C_{1-18}$ hydrocarbyl that is substituted with one or more heteroatoms or is unsubstituted; and $L_7$ is $C_{1-18}$ hydrocarbyl that is substituted with one or more heteroatoms or is unsubstituted.

In some embodiments, $L_6$ and $L_7$ are $C_{1-18}$ alkyl groups.

In some embodiments, $L_6$ is —$CH_3$ or —$(CH_2)_9$—$CH_3$; and $L_7$ is —$CH_3$ or —$CH_2CH_3$.

In some embodiments, $L_3$ is

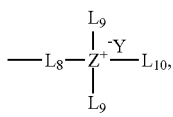

where Z is N or P; Y is halogen; $L_8$ is a $C_{1-18}$ hydrocarbyl that is substituted with one or more heteroatoms or is unsubstituted; $L_9$ is $C_{1-18}$ hydrocarbyl that is substituted with one or more heteroatoms or is unsubstituted; and $L_{10}$ is $C_{1-18}$ hydrocarbyl that is substituted with one or more heteroatoms or is unsubstituted.

In some embodiments, $L_8$ is —$(CH_2)_u$—, where u=0-18; $L_9$ is —$CH_3$ or phenyl that is unsubstituted or substituted with one or more heteroatoms; and $L_{10}$ is —$(CH_2)_v$—$CH_3$, wherein v=0-17.

In some embodiments, $L_3$ is

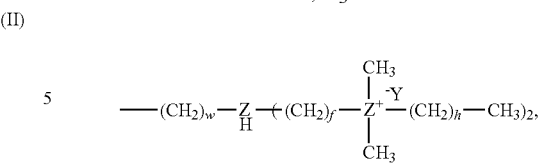

where Y is halogen; Z is N or P; w=0-18; f=0-18; and h=0-17.

In some embodiments, w=2; f=1, 2 or 18; and h=0, 9 or 11.

In some embodiments, X is O.

In some embodiments, $L_3$ is

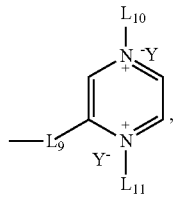

where Y is halogen; $L_9$ is a $C_{1-18}$ hydrocarbyl that is substituted with one or more heteroatoms or is unsubstituted; $L_{10}$ is a $C_{1-18}$ hydrocarbyl that is substituted with one or more heteroatoms or is unsubstituted; and $L_{11}$ is a $C_{1-18}$ hydrocarbyl that is substituted with one or more heteroatoms or is unsubstituted.

In some embodiments, $L_{10}$ is —$(CH_2)_i$—$CH_3$, where i is 0-17; and $L_{11}$ is —$(CH_2)_j$—$CH_3$, where j is 0-17.

In some embodiments, $L_{10}$ and $L_{11}$ are the same.

In some embodiments, $L_1$ is Cl.

For illustration purposes, a plurality of compounds having the general formulas (I) or (II) are listed in Table 1, Table 2, and Table 3. It should be noted that the structure of the compounds are not limited by thoses mentioned in the present disclosure.

Another aspect of the present disclosure provides a preparation method of the compound. The preparation method has a simple route and for each step, the reaction process is relatively simple. The preparation method involves a substitution reaction. The preparation method does not require highly toxic reagents such as aromatic hydrocarbon, and thus the preparation method is relatively safe to be implemented.

The preparation method of the present disclosure compound (I) may include the following operations.

A compound having the structure shown in the general formula (III) is reacted with HX—$R_3$ to obtain the compound (I);

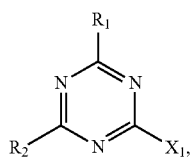

(II)

$X_1$ is halogen (such as Cl, Br or I);

Preferably, the compound of the structure shown in the general formula (III) and the reaction of HX—$R_3$ are carried out under the presence of a Lewis base, which is preferably selected from the group consisting of alkali metal, inorganic base of alkaline earth metal, and organic base of alkaline earth metal.

The above reaction mainly utilizes a nucleophilic substitution reaction between a compound of the structure shown in the general formula (III) and HX—R$_3$. A reaction solvent and an auxiliary/catalyst may be advantageous for the nucleophile to attack or promote the formation of a positive ion by the triazine ring. When the R$_3$ of the synthesized compound (I) is different, the reaction conditions may be different.

HX—R$_3$ may include a quaternary ammonium salt/quaternary phosphorus salt produced by reacting a tertiary amine/tertiary phosphine with halogenated hydrocarbon.

Preferably, the compound of the structure shown in the general formula (III) and the reaction of HX—R$_3$ may be carried out under the presence of a Lewis base and an organic solvent. The Lewis base may cause the triazine ring to form a positive ion. The selection of Lewis base may be generally based on the properties (e.g., hydrophilicity and the lipophilicity) of the HX—R$_3$. If the HX—R$_3$ is hydrophilic, the inorganic base may be used, and the inorganic base may be selected from a strong base of an alkali metal or an alkaline earth metal, a carbonate of an alkali metal or an alkaline earth metal, a hydrogen carbonate of an alkali metal or an alkaline earth metal, or the like; if an organic solvent is used, an organic base such as one or more of N, N-diisopropylethylamine, triethylamine, trimethylamine and tributylamine is usually used.

In some embodiments, the inorganic base is selected from one or more of the group consisting of sodium hydroxide, potassium hydroxide, magnesium hydroxide, calcium hydroxide, potassium carbonate, potassium hydrogencarbonate, sodium carbonate, and sodium hydrogencarbonate.

In some embodiments, the organic tertiary amine is selected from the group consisting of one or more mixtures of N, N-diisopropyl-ethylamine, trimethylamine, triethylamine, N, N-dimethyl-n-octylamine, N, N-dimethylaniline, N, N-dimethyl-dodecylamine, N, N-dimethyl-dodecylamine, N, N-dimethyl-hexadecylamine, N, N-dimethyl-octadecylamine, N, N-dimethyl-decylamine, dimethylaminoethyl methacrylate, diethylaminoethyl methacrylate, and combinations thereof.

When R$_3$ is

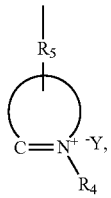

the method may be performed in two steps:
  producing HX—R$_3$ by the reaction of

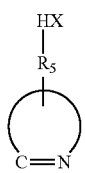

and Y—R$_4$; and
  reacting the compound having the structure shown in the general formula (III) with HX—R$_3$ to produce the compound (I).

Where,

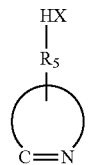

may be a heteroatom (O, N, S) substituted pyridine, furan, imidazole, pyrazine or the like, such as 4-indolylpyridine, 2, 6-dimethyl-4-aminopyridine, 1-(3-aminopropyl)imidazole, 4-(hydroxymethyl)imidazole, 2-pyrazinylethanethiol, 2-pyrazinemethanol or histamine, which is not limited to the above mentioned compounds.

When the structural formula of the compound is:

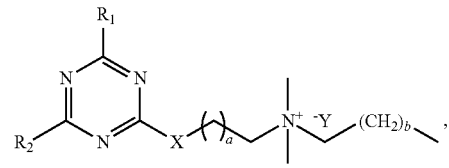

the preparation method may be performed in two steps:
  generating HX—R$_3$ by reaction of

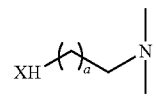

and Y—(CH$_2$)$_b$CH$_3$; and
  reacting the compound having the structure shown in the general formula (III) is with HX—R$_3$ to produce the compound (I).

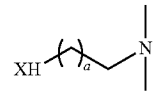

may be N, N-dimethyl-ethanolamine, N, N-dimethyl-ethylenediamine, N, N-diethyl-ethanolamine, N, N-diisopropyl-ethanolamine, N, N-di-n-butyl-ethanolamine, N, N-di-n-pentyl-ethanolamine or N, N-dicyclohexyl-ethanolamine, but is not limited to the above mentioned compounds.

When the R$_3$ is

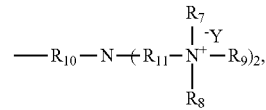

the preparation method is performed in three steps:
  producing

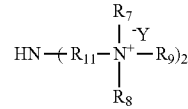

by the reaction of

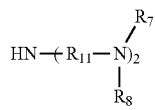

and Y—R$_9$;
producing HX—R$_3$ by the reaction of

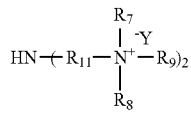

and HX—R$_{10}$-Q; Q is halogen, preferably Br, Cl or I; X is preferably O, S, NH. If X is NH, the —NH$_2$ group needs to be firstly protected before the reaction, and then de-protected after the reaction is completed. Exemplary groups that can be used to protect the —NH$_2$ group include carbamazepine (Cbz), t-butyloxycarboryl (t-BOC), fluorenylmethyloxycarbonyl (Fmoc), or the like.

The compound having the structure shown in the general formula (III) is reacted with HX—R$_3$ to produce the compound (I).

When the R$_3$ is

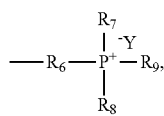

the preparation method is performed in two steps:
generating HX—R$_3$ by reaction of

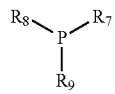

and Y—R$_6$—HX;
reacting the compound having the structure shown general formula (III) with HX—R$_3$ to produce the compound (I).

In order to more clearly describe the mechanisms in the present disclosure, synthesis principles of some compounds involved in the present disclosure are described as follows. Cyanuric chloride is used as an example. The synthesis route of cyanuric chloride is the same as that of cyanuric chloride if replacing "cyanuric cyanide" with "substituted cyanuric chloride".

The principle of synthesis of imidazole quaternary ammonium salts is:

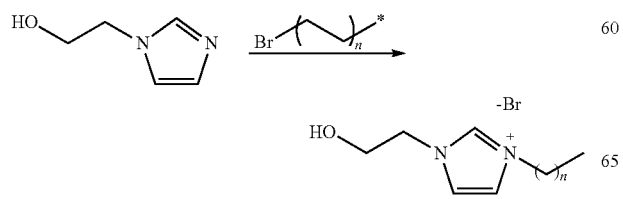

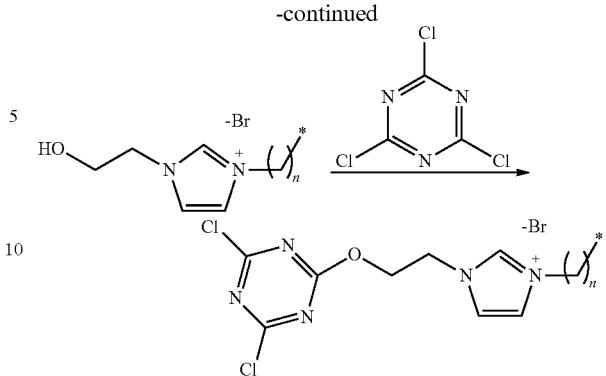

n=0-17, preferably 0, 1, 3, 5, 7, 9, 11, 13, or 17.
The principles of the synthesis of the biquaternary ammonium salt are:

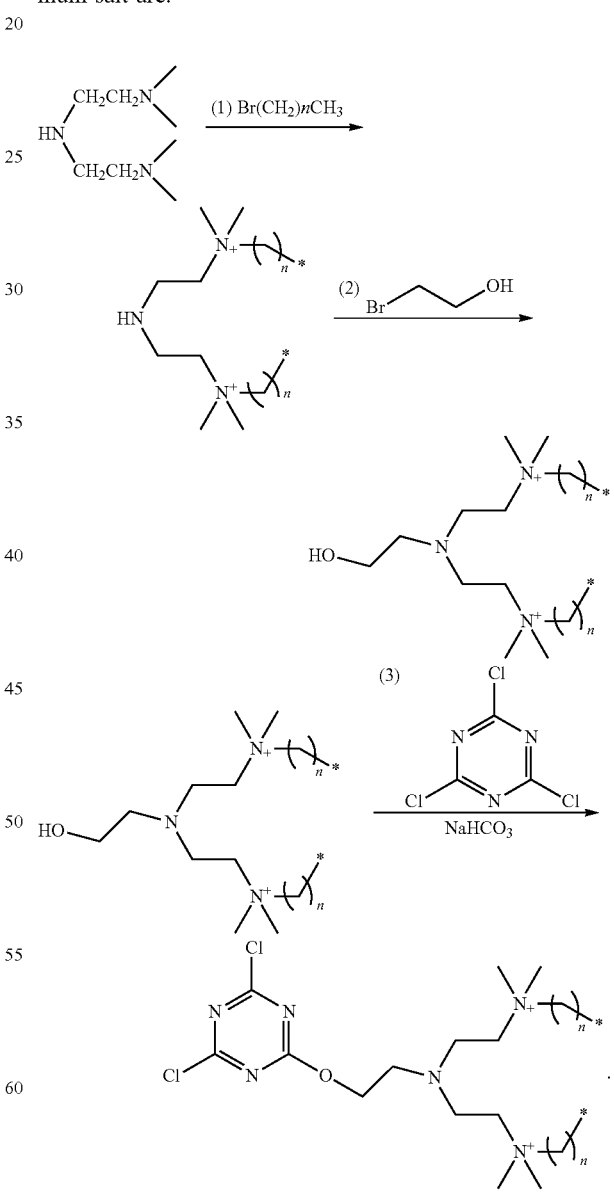

where n is a natural number from 0 to 17, and n may be 0, 1, 3, 5, 7, 9, 11, 13, 15, or The principles of the synthesis of quaternary phosphonium salt is:

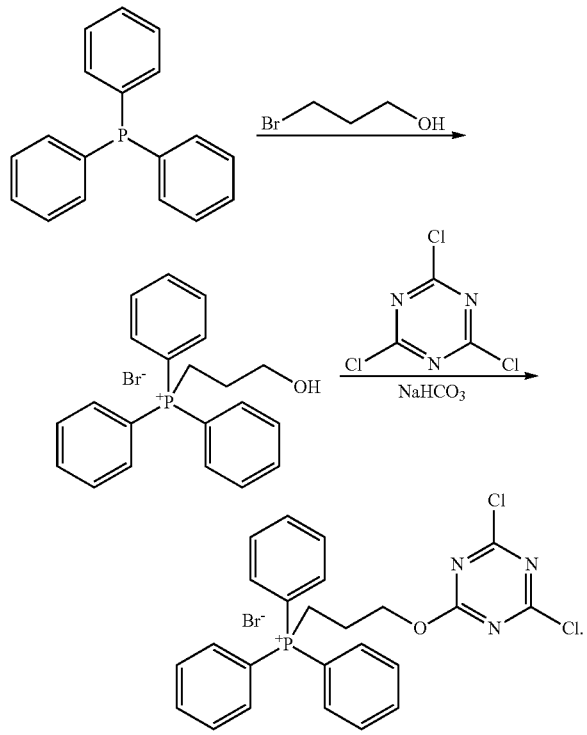

Methods for preparing the compound having the general formula (II) may be similar to the methods for preparing the compound having the general formulas (I), and is not repeated herein. More details regarding the method for preparing the compound having the general formulas (I) or (II) may be found elsewhere in the present disclosure, for example, in the EXAMPLES section.

Another aspect of the present disclosure provides an anti-microbial or an-mite product. The product may include the compound. In some embodiments, the product may be present in the form of, for example, granules, powder, micellas, solution, suspension, emulsion, or the like, or any combination thereof. In some embodiments, the product may be transported and/or stored in an intermediate formulation. For example, the intermediate formulation may be powder or granules, and the product may be dissolved in an appropriate solvent before usage. As another example, the intermediate formulation may be a liquid with a relatively high concentration (e.g., 80%, 90%) of the compound. The product may be diluted using an appropriate solvent before usage.

In some embodiments, the product may include one or more auxiliary components. For example, the one or more auxiliary components may include cosolvents, pH adjusting agents, hydrophobicizers, oleophobicizers, binders, crosslinks, surfactants, softeners, dyes, flame retardants, textiles dyes, sewability improvers, and combinations thereof.

In some embodiments, the pH adjusting agents may include Lewis base, such as sodium carbonate, sodium hydrogencarbonate, potassium carbonate, potassium hydrogencarbonate, triethylamine, trimethylamine, tributylamine, or the like, or any combination thereof.

In some embodiments, the surfactants may include stearic acid, sodium dodecylbenzene sulfonate, sodium hexadecyl sulfonate, sodium stearyl sulfonate, sodium cetyl carboxylate, sodium lauryl sulfate, sodium hexadecyl sulfate, sodium lauryl carboxylate, lecithin, fatty acid glycerides, or the like, or any combination thereof.

In some embodiments, the product is present in the form of a liquid. The product may include a solvent for solving the compound. For instance, the solvent may include water, dimethyl sulfoxide, chloroform, ether, ketone, ester, nitrile, amide, aromatic compound, or the like, or any combinations thereof.

In some embodiments, the ether may be selected from the group consisting of tetrahydrofuran, 1, 4-dioxane, ethylene glycol dimethyl ether, and combinations thereof.

In some embodiments, the ketone may be selected from the group consisting of acetone, methyl ethyl ketone, cyclohexanone, acetophenone, phorone, and combinations thereof.

In some embodiments, the aromatic compound may be selected from the group consisting of toluene, pyridine, imidazole, and combinations thereof.

In some embodiments, the ester may be selected from the group consisting of ethyl acetate, n-butyl acetate, n-propyl acetate, ethyl formate, methyl formate, and combinations thereof.

In some embodiments, the nitrile may be selected from the group consisting of acetonitrile, propionitrile, benzonitrile, and combinations thereof.

In some embodiments, the amide may be selected from the group consisting of N, N-dimethyl-acetamide, N, N-dimethyl-formamide and N, N-dimethyl-pyrrolidone.

In some embodiments, the cosolvent may be consisting of water, dimethyl sulfoxide, ether, ketone, ester, nitrile, amide aromatic compound, and combinations thereof.

In some embodiments, the ether in the cosolvent may be selected from the group consisting of tetrahydrofuran, 1, 4-dioxane, ethylene glycol dimethyl ether, and combinations thereof.

In some embodiments, the ketone in the cosolvent may be selected from the group consisting of acetone, methyl ethyl ketone, cyclohexanone, acetophenone, phorone, and combinations thereof.

In some embodiments, the aromatic compound in the cosolvent may be selected from the group consisting of toluene, pyridine, imidazole, and combinations thereof.

In some embodiments, the ester in the cosolvent may be selected from the group consisting of ethyl acetate, n-butyl acetate, n-propyl acetate, ethyl formate, methyl formate, and combinations thereof.

In some embodiments, the nitrile in the cosolvent may be selected from the group consisting of acetonitrile, propionitrile, benzonitrile, and combinations thereof.

In some embodiments, the amide in the cosolvent may be selected from the group consisting of N, N-dimethylacetamide, N, N-dimethylformamide, N, N-dimethylpyrrolidone, and combinations thereof.

In some embodiments, the content of the compound (I) in the product is 0.01 to 15% of the product by weight, preferably 0.05 to 10% of the product by weight, more preferably 0.1 to 5% by weight.

In some embodiments, the pH of the product is 8-11, preferably 8, 8.5, 9, 9.5, 10, 10.5 or 11.

In some embodiments, the content of the surfactant in the product is 0.01 to 2 wt % (by weight), preferably 0.05 to 0.08 wt %.

In some embodiments, the content of the cosolvent in the product is 0 to 12 wt %, preferably 0.1 to 10 wt %.

In some embodiments, the product may be used to kill microorganisms and/or mites. In some embodiments, the microorganisms may include bacteria, fungi, virus, or the like, or any combination thereof. In some embodiments, the microorganisms may include Gram-negative bacteria (*E. coli*) and/or Gram-positive bacteria (*Staphylococcus aureus*). For example, the microorganisms that can be killed by the product may include at least one of *Escherichia coli, Staphylococcus aureus, Candida albicans*, or *Aspergillus niger*. In some embodiments, the mites that can be killed by the product may include at least one of dust mites, fur mites, or parasitic mites.

In some embodiments, the product may be an anti-microbial or anti-mite agent for treating materials such as wood, synthetic polymers, fibers, cloth, paper, rubber, glass, or metal. The compound in the product may improve anti-microbial or anti-mite abilities of the materials. For example, the product may be a finishing agent for treating textiles, fibers, and/or yarns. Merely by way of example, the product may be a finishing liquid which may be used to soak the textiles, fibers, and/or yarns for a predetermined period of time.

In some embodiments, the product may include a solid support formed by materials such as wood, synthetic polymers, fibers, cloth, paper, rubber, glass, or metal. The compound may have been applied on the solid support, for example, on the surface and/or in an internal portion of the solid support. In some embodiments, the compound may react with —OH and —$NH_2$ groups and thereby become chemically bonded to the solid support. In some embodiments, the product may be textiles that includes the compound. For example, the solid support may be textiles, such as gloves, clothes, surgical masks, underwear. The textiles may be made of cotton, silk, wool, cellulose, linen, acetate, flax, or the like, or any combination thereof.

In some embodiments, the structure and/or appearance of at least a portion of the textiles may be affected by microorganisms. For instance, mycete may affect the color of the textiles and bring unpleasant odour. As another example, some microorganisms may degrade the structure of the materials of the textiles, such as silk, wool, and cause damage to the textiles (e.g., by forming holes on the textiles). The product may be used to protect the textiles from the negative impact of the microorganisms, and thus it may be easier to store the textiles. In some embodiments, the compound may be used to decrease the number count of some pathogenic microorganisms or mites in the textiles, which may protect people wearing or carrying the textiles against the pathogenic microorganisms, such as, *E. coli* and *S. aureus*. In some embodiments, the anti-microbial rate of the compound may be >99.9% (e.g., as shown in Example 22 and/or Example 23).

In some embodiments, the compound may be chemically bonded to the surface of the solid support. For example, the compound may react with —OH and —$NH_2$ groups on the surface of the solid support. The chemical bond may improve the durability of the compound against washing. Thus, a long-lasting anti-microbial and/or anti-mite effect may be achieved by the product.

Another aspect of the present disclosure provides a use of the compound for anti-microbial or anti-mite applications, or anti-microbial and/or anti-mite product preparation. The use of the compound may have many advantages. For example, the bonding force between the compound and the fiber is relatively strong; the anti-microbial effect can remain after a plurality of washing processes; the cost is relatively low; the use of the compound is relatively convenient; and the use of the compound in a finishing process (e.g., for textiles) has no exhaust gas discharge.

In some embodiments, the microorganisms may include bacteria, fungi, virus, or the like, or any combination thereof. For example, the microorganisms that can be killed by the product may include at least one of *Escherichia coli, Staphylococcus aureus, Candida albicans*, or *Aspergillus niger*.

In some embodiments, the mites that can be killed by the product may include at least one of dust mites, fur mites, or parasitic mites.

Another aspect of the present disclosure provides a method of using the compound for killing microorganisms or mites.

In some embodiments, the method may include applying a product that includes the compound to a target object. For example, the product may be used to contact the target object. The product may be present in the form of, for example, granules, powder, micellas, solution, suspension, emulsion, or the like, or any combination thereof.

In some embodiments, the target object may include at least one of wood, synthetic polymers, fibers, cloth, paper, rubber, glass, or metal.

In some embodiments, the target object is selected from the group consisting of textiles, fibers, yarns, food packaging materials, medical devices, or the like, or any combination thereof.

In some embodiments, using the product to contact the target object may include a soaking process, a padding process, a spraying process, a brushing-coating process, an electrospinning process, or the like, or any combination thereof.

In some embodiments, after the product contacts with the target object, one or more additional processes may be performed to cause the compound according to the general formula (I) or (II) to be relatively firmly connected to the surface of the target object. For instance, a heating process may be performed to facilitate a chemical reaction between the compound and functional groups on the surface of the target object (e.g., —OH and —$NH_2$ groups). Additionally or alternatively, the heating process may facilitate the solvent in the product to volatilize and cause a coating layer to be formed on the surface of the target object.

In some embodiments, the method may be an anti-microbial finishing method for textiles, which may have some advantages. For example, the process is simple and can be automized. As used herein, the term "finishing method" refers to one or more processes for treating textiles that have been shaped to improve one or more properties of the textiles. For example, the method of using the product provided by the present disclosure may improve the anti-microbial and/or anti-mite properties of the textiles.

Merely by way of example, the finishing method for improving the anti-microbial and/or anti-mite properties of textiles may include the following operations: soaking the textiles in the product (e.g., an anti-microbial finishing agent in the liquid form) described above, and then heating the textiles to shape.

In some embodiments, the product (e.g., textiles) may be soaked in the product (diluted or undiluted) for a predetermined time period.

For example, the predetermined time period may include 1 second (s) to 60 min, preferably 1 s, 5 s, 10 s, 20 s, 30 s, 60 s, 5 min, 10 min, 15 min, 20 min, 30 min or 60 min.

The weight of the anti-microbial finishing liquid for soaking is 5 to 50 times, more preferably 10, 15, 20, 25 or 30 times the weight of the textiles.

Preferably, the heating temperature is 60 to 150° C., more preferably 80° C., 85° C., 90° C., 95° C., 100° C. or 105° C.

Compared with some existing methods, the present disclosure may achieve one or more of the following technical effects:
(1) providing a compound which can be used for anti-microbial finishing of textiles, the compound being able to chemically react with groups such as hydroxyl groups and amino groups on the surface of the material, and can be firmly bonded to the material; under the premise of generally no adverse effect on the physical properties such as mechanical properties, moisture permeability and color, the surface of the material can achieve broad-spectrum, long-lasting, and highly effective anti-microbial/anti-mite properties;
(2) the compound bond to the materials is not released in water from the materials, and thus the compound may be non-toxic and non-irritating to the skin; normal washing processes may not have a significant effect on the antimicrobial/anti-mite properties of the materials;
(3) the finishing process for textiles, fibers, or yarns may be carried out using a common immersion-rolling-drying process or a spray-spinning-drying process without generating waste water or waste gas;
(4) the finishing agent may be stored and transported in the form of a product with a relatively high concentration (e.g., 50%) or even as a pure product, which is more environmentally friendly and more energy efficient.

The present disclosure is further described according to the following examples, which should not be construed as limiting the scope of the present disclosure.

EXAMPLES

Methods

The preparation process of the product (i.e., the anti-microbial and anti-mite compound) according to Examples 1 to 16 below is carried out in two steps, and the reaction route is as follows:

A+B→Intermediate I

Intermediate I+D→E

The structural formulas of reactants A and B, Intermediate I, reactant D and product E in the examples are shown in Tables 1 and 2, respectively.

TABLE 1

| Embodiment | reactant A | reactant B | Intermediate I |
|---|---|---|---|
| 1 | HO-CH$_2$CH$_2$-N(CH$_3$)$_2$ | Br-CH$_2$CH$_2$-(CH$_2$)$_6$-CH$_3$ | HO-CH$_2$CH$_2$-N$^+$(CH$_3$)$_2$-CH$_2$CH$_2$-(CH$_2$)$_6$-CH$_3$ Br$^-$ |
| 2 | HO-CH$_2$CH$_2$-N(CH$_3$)$_2$ | Br-CH$_2$CH$_2$-(CH$_2$)$_{16}$-CH$_3$ | HO-CH$_2$CH$_2$-N$^+$(CH$_3$)$_2$-CH$_2$CH$_2$-(CH$_2$)$_{16}$-CH$_3$ Br$^-$ |
| 3 | H$_2$N-CH$_2$CH$_2$-N(CH$_3$)$_2$ | BrCH$_3$ | H$_2$N-CH$_2$CH$_2$-N$^+$(CH$_3$)$_3$ Br$^-$ |
| 4 | HO-(CH$_2$)$_{17}$-N(CH$_3$)$_2$ | BrCH$_3$ | HO-(CH$_2$)$_{17}$-N$^+$(CH$_3$)$_3$ Br$^-$ |
| 5 | HO-CH$_2$-N(CH$_3$)$_2$ | BrCH$_3$ | HO-CH$_2$-N$^+$(CH$_3$)$_3$ Br$^-$ |
| 6 | HO-CH(CH$_3$)-CH$_2$-N(CH$_3$)$_2$ | Br-CH$_2$CH$_2$-(CH$_2$)$_6$-CH$_3$ | HO-CH(CH$_3$)-CH$_2$-N$^+$(CH$_3$)$_2$-CH$_2$CH$_2$-(CH$_2$)$_6$-CH$_3$ Br$^-$ |
| 7 | imidazole-N-CH$_2$CH$_2$CH$_2$-NH$_2$ | Br-CH$_2$CH$_2$-(CH$_2$)$_{12}$-CH$_3$ | C$_{14}$H$_{29}$-N$^+$-imidazole-N-CH$_2$CH$_2$CH$_2$-NH$_2$ Br$^-$ |
| 8 | 4-pyridyl-CH$_2$CH$_2$-OH | Br-CH$_2$CH$_2$-(CH$_2$)$_8$-CH$_3$ | C$_{10}$H$_{21}$-N$^+$(pyridyl)-CH$_2$CH$_2$-OH Br$^-$ |

TABLE 1-continued

| Embodiment | reactant A | reactant B | Intermediate I |
|---|---|---|---|
| 9 | 4-(aminomethyl)pyridine | ICH₃ | N-methyl-4-(aminomethyl)pyridinium iodide |
| 10 | histamine (4-(2-aminoethyl)imidazole) | Br—(CH₂)₆—CH₃ (1-bromooctane) | 3-octyl-4-(2-aminoethyl)imidazolium bromide |
| 11 | 1-(2-hydroxyethyl)imidazole | Br—(CH₂)₁₅—CH₃ | 1-(2-hydroxyethyl)-3-hexadecylimidazolium bromide |
| 12 | 1-(2-hydroxyethyl)imidazole | CH₃Br | 1-(2-hydroxyethyl)-3-methylimidazolium bromide |
| 13 | 1-(17-hydroxyheptadecyl)imidazole | CH₃Br | 1-(17-hydroxyheptadecyl)-3-methylimidazolium bromide |
| 14 | 1-(3-aminopropyl)imidazole | CH₃Br | 1-(3-aminopropyl)-3-methylimidazolium bromide |
| 15 | 4-(hydroxymethyl)pyridine | CH₃Br | 1-methyl-4-(hydroxymethyl)pyridinium bromide |
| 16 | 2-(pyrazin-2-yl)ethanethiol | C₁₂H₂₅Br | 1,4-didodecyl-2-(2-mercaptoethyl)pyrazinium dibromide |

TABLE 2

| Embodiment | Intermediate I | reactant D | product E |
|---|---|---|---|
| 1 | (2-hydroxyethyl)dimethyl(heptyl)ammonium bromide | cyanuric chloride (2,4,6-trichloro-1,3,5-triazine) | 2-((4,6-dichloro-1,3,5-triazin-2-yl)oxy)ethyl-dimethyl-heptyl-ammonium bromide |

TABLE 2-continued

| Embodiment | Intermediate I | reactant D | product E |
|---|---|---|---|
| 2 | HO-CH2CH2-N+(CH3)2-(CH2)16CH3 Br− | 2,4,6-trichloro-1,3,5-triazine | 4,6-dichloro-1,3,5-triazin-2-yl-O-CH2CH2-N+(CH3)2-(CH2)16CH3 Br− |
| 3 | H2N-CH2CH2-N+(CH3)3 Br− | 2,4,6-trichloro-1,3,5-triazine | 4,6-dichloro-1,3,5-triazin-2-yl-NH-CH2CH2-N+(CH3)3 Br− |
| 4 | HO-(CH2)17-N+(CH3)3 Br− | 2,4,6-trichloro-1,3,5-triazine | 4,6-dichloro-1,3,5-triazin-2-yl-O-(CH2)17-N+(CH3)3 Br− |
| 5 | HO-CH2-N+(CH3)3 Br− | 2,4,6-trichloro-1,3,5-triazine | 4,6-dichloro-1,3,5-triazin-2-yl-O-CH2-N+(CH3)3 Br− |
| 6 | HO-CH(CH3)-CH2-N+(CH3)2-(CH2)6CH3 Br− | 2,4,6-trichloro-1,3,5-triazine | 4,6-dichloro-1,3,5-triazin-2-yl-O-CH(CH3)-CH2-N+(CH3)2-(CH2)6CH3 Br− |
| 7 | 1-C14H29-3-(3-aminopropyl)imidazolium Br− | 2,4-dichloro-6-methyl-1,3,5-triazine | 1-C14H29-3-[3-(4-chloro-6-methyl-1,3,5-triazin-2-ylamino)propyl]imidazolium Br− |
| 8 | 1-C10H21-4-(2-hydroxyethyl)pyridinium Br− | 2,4-dibromo-6-chloro-1,3,5-triazine | 1-C10H21-4-{2-[(4-bromo-6-chloro-1,3,5-triazin-2-yl)oxy]ethyl}pyridinium Br− |
| 9 | 1-methyl-4-(aminomethyl)pyridinium I− | 2,4-dichloro-6-nitro-1,3,5-triazine | 1-methyl-4-{[(4-chloro-6-nitro-1,3,5-triazin-2-yl)amino]methyl}pyridinium I− |

TABLE 2-continued

| Embodiment | Intermediate I | reactant D | product E |
|---|---|---|---|
| 10 | imidazole with C8H17, Br⁻, CH2CH2NH2 | cyanuric chloride | triazine-NH-ethyl-imidazolium C8H17 Br⁻ with two Cl |
| 11 | HO-ethyl-imidazolium-C18H37 Br⁻ | cyanuric chloride | triazine(Cl,Cl)-O-ethyl-imidazolium-C18H37 Br⁻ |
| 12 | HO-ethyl-imidazolium-CH3 Br⁻ | 2,4-dichloro-6-methyl-triazine | methyl-triazine(Cl)-O-ethyl-imidazolium-CH3 Br⁻ |
| 13 | HO-(CH2)17-imidazolium-CH3 Br⁻ | cyanuric chloride | triazine(Cl,Cl)-O-(CH2)17-imidazolium-CH3 Br⁻ |
| 14 | methyl-imidazolium-(CH2)3-NH2 Br⁻ | cyanuric chloride | methyl-imidazolium-(CH2)3-NH-triazine(Cl,Cl) Br⁻ |
| 15 | HO-CH2-pyridinium-CH3 Br⁻ | cyanuric chloride | triazine(Cl,Cl)-O-CH2-pyridinium-CH3 Br⁻ |
| 16 | pyrazinium di-C12H25 2Br⁻ with CH2CH2SH | cyanuric chloride | pyrazinium di-C12H25 2Br⁻ with CH2CH2-S-triazine(Cl,Cl) |

The specific preparation process of each of embodiments 1-16 are as follows.

Example 1

1.35 g (15 mmol) of N, N-dimethyl-ethanolamine (DMEA, Compound A) and 4.35 g (22.5 mmol) of bromooctane (Compound B) were added to a round bottom-bottom flask, and it was placed in an oil bath at 45° C. for reaction of 2 h. 12 mL of acetone was added as a solvent to the round bottom-bottom flask, followed by backflow for 12 h. After the reaction was completed, the solvent was evaporated under reduced pressure at 60° C. to obtain a white solid, which was washed several times with anhydrous petroleum ether, and dried in a vacuum oven to obtain Intermediate I, which was stored in a bottle for use. The yield of the intermediate was 92%, and the NMR data were: 1H NMR (600 MHz, D$_2$O) δ 3.92 (tt, J=4.9, 2.2 Hz, 2H), 3.41-3.33 (m, 2H), 3.29-3.22 (m, 2H), 3.01 (s, 6H), 1.66 (ddd, J=15.0, 9.4, 5.6 Hz, 2H), 1.32-1.10 (m, 10H), 0.75 (t, J=6.8 Hz, 3H).

1.42 g (5 mmol) of Intermediate I and 0.8 g of sodium carbonate were dissolved in 10 mL of deionized water to prepare a solution to be added to the dropping funnel for use; 1.2 g (4.9 mmol) of cyanuric chloride (i.e., Compound D) was dissolved in 30 mL of tetrahydrofuran and the solution was added to the round bottom-bottom flask and stirred at 40° C. for 5 min; the solution in the dropping funnel was dropped into the round-bottom flask at the dropping speed of 30 min. After the addition, the reaction was continued for 30 min while monitored by TLC; after the completion of the reaction, the mixture was extracted with methylene chloride. The organic phase was dried using anhydrous sodium sulfate and the mixture was dried via rotary drying to produce a white solid. The yield of this product was 89% and the NMR data were: 1H NMR (600 MHz, DMSO-d6) 3.80 (t, J=5.0 Hz, 2H), 3.42-3.35 (m, 2H), 3.37-3.31 (m, 2H), 3.08 (s, 6H), 1.70-1.61 (m, 2H), 1.32-1.19 (m, 10H), 0.85 (t, J=7.0 Hz, 3H).

Example 2

1.35 g (15 mmol) of N, N-dimethyl-ethanolamine (DMEA, Compound A) and 9.13 g (22.5 mmol) of Compound B (bromooctadecane) were added to the round-bottom flask, and the round-bottom flask was placed in an oil bath at 35° C. for reaction of 5 hours. 20 mL of ethanol was added as a solvent to the round-bottom flask, followed by backflow for 8 h; after the reaction was completed, the solvent was dried via rotary drying under reduced pressure at 40° C. to produce a white solid, which was washed several times with anhydrous diethyl ether and dried in a vacuum oven to obtain intermediate (quaternary ammonium alcohol, i.e., Intermediate I) and stored in a bottle for use. The yield of the intermediate was 92%, and the NMR data were: 1H NMR (600 MHz, D$_2$O) δ 3.92 (tt, J=4.9, 2.2 Hz, 2H), 3.41-3.33 (m, 2H), 3.29-3.22 (m, 2H), 3.01 (s, 6H), 1.66 (ddd, J=15.0, 9.4, 5.6 Hz, 2H), 1.32-1.10 (m, 30H), 0.75 (t, J=6.8 Hz, 3H).

4.22 g (10 mmol) of intermediate (quaternary ammonium alcohol) and 1.3 g (10 mmol) N, N-diisopropylethylamine were dissolved in 20 mL of dichloromethane, and the solution was added to a dropping funnel; 1.91 g (10 mmol) of cyanuric chloride (i.e., Compound D) was weighed and dissolved in 50 mL of dichloromethane in a round-bottom flask and the mixture was stirred at 30° C. for 30 min; the solution in the dropping funnel was dropped into the round-bottom flask, and the dropping rate was 1 h. After the addition, the reaction was continued overnight while monitored by TLC; after the end of the reaction, flash column chromatography gave a pure product with a yield of 76%. The NMR data were: 1H NMR (600 MHz, DMSO-d6) 3.80 (t, J=5.0 Hz, 2H), 3.42-3.35 (m, 2H), 3.37-3.31 (m, 2H), 3.08 (s, 6H), 1.70-1.61 (m, 2H), 1.32-1.19 (m, 30H), 0.85 (t, J=7.0 Hz, 3H).

Example 3

0.89 g of N, N-dimethyl-ethylenediamine (Compound A) and 1.44 g of methyl bromide (Compound B) were added to a round-bottom flask, and the round-bottom flask was placed in a 65° C. constant temperature oil bath for reaction of 1 h; 20 mL of propanol was added as a solvent to the round-bottom flask, and then the reaction was continued for 15 h; after the reaction was completed, the solvent was dried via a rotary drying method under reduced pressure at 40° C. to produce a white solid, which was washed several times with tetrahydrofuran and dried in a vacuum oven to obtain Intermediate I (quaternary ammonium amine); the Intermediate I was stored in a bottle for use. The yield of the intermediate was 95%, and the NMR data were: 1H NMR (600 MHz, D$_2$O) 3.52 (t, 2H), 3.30 (s, 9H), 3.09 (t, 2H).

1.83 g of Intermediate I (quaternary ammonium amine) and 2.6 g of N, N-diisopropyl-ethylamine were dissolved in 20 mL of dichloromethane, and the solution was added to the dropping funnel; 2.0 g of cyanuric chloride (CC) was weighed and dissolved in 30 mL of dichloromethane in a round-bottom flask and the mixture was stirred at room temperature for 15 min; the solution in the dropping funnel was dropped into the round-bottom flask, the dropping speed was 2 h, and after the addition, the reaction was continued for 1 h, and the TLC monitored the reaction; after the end of the reaction, the solvent was removed under reduced pressure in vacuo to produce a product (yield: 83%, NMR data: 1H NMR (600 MHz, Chloroform-d) 3.47-3.52 (m, 4H), 3.31 (s, 9H).

Example 4

3.12 g (10 mmol) of N, N-dimethyloctadecylamine (Compound A) and 1.45 g (15 mmol) of methyl bromide (Compound B) were added to the round-bottom flask. The reaction was carried out in an oil bath at 65° C. for reaction of 2 h. 12 mL of isopropanol was added as a solvent to the round-bottom flask, followed by backflow for 12 h; after the reaction was completed, the solvent was evaporated under reduced pressure at 60° C. to obtain a white solid, which was washed several times with anhydrous petroleum ether, and dried in a vacuum oven to obtain Intermediate I; the Intermediate I was stored in a bottle for use. The yield of the intermediate was 89%, and the NMR data were: 1H NMR (600 MHz, D$_2$O) 3.62 (t, 2H), 2.83 (s, 9H), 2.2 (t, 2H), 1.3-1.58 (m, 32H).

3.98 g of Intermediate I (quaternary ammonium alcohol) and 2.6 g of N, N-diisopropylethylamine were dissolved in 20 mL of tetrahydrofuran, and the solution was added to the dropping funnel; 2.0 g of cyanuric chloride (CC) was dissolved in 30 mL of tetrahydrofuran in a round-bottom flask and stirred at room temperature for 15 min; the solution in the dropping funnel dropped into the round-bottom flask, the dropping speed was 2 h, and after the addition, the reaction was carried out for 1 h, and the TLC monitored the reaction; after the reaction was completed, the solvent was removed under reduced pressure in vacuo to produce a product. The yield of the product was 78%, and the nuclear magnetic resonance data were: 1H NMR (600 MHz, Chloroform-d) 3.82 (t, 2H), 2.83 (s, 9H), 2.2 (t, 2H), 1.3-1.58 (m, 32H).

Example 5

0.75 g (10 mmol) of N, N-dimethyl-methanolamine (Compound A) and 1.45 g (15 mmol) of methyl bromide (Compound B) were added to the round-bottom flask, and it was placed in an oil bath at 45° C. for reaction of 2 h. 12 mL of methanol was added as a solvent to the round-bottom flask, followed by backflow for 12 h; after the reaction was completed, the solvent was evaporated under reduced pressure at 60° C. to obtain a white solid, which was washed several times with anhydrous petroleum ether, and dried in a vacuum oven to obtain Intermediate I, which was stored in a bottle for use. The yield of the intermediate was 97%, and the NMR data were: 1H NMR (600 MHz, D$_2$O) 5.42 (s, 2H), 3.30 (s, 9H).

0.85 g (5 mmol) of Intermediate I and 0.8 g of sodium carbonate were dissolved in 10 mL of deionized water to prepare a solution to be added to the dropping funnel for use; 1.2 g (4.9 mmol) of cyanuric chloride (i.e., Compound D) was weighed and dissolved in 30 mL of tetrahydrofuran and the solution was added to the round-bottom flask, and the mixture was stirred at 40° C. for 5 min; the solution in the dropping funnel was dropped into the round-bottom flask, and the dripping speed was controlled to 30 min. After the addition, the reaction was continued for 30 min while monitored by TLC; after the completion of the reaction, the mixture was extracted with methylene chloride for three times. The organic phase was dried using anhydrous sodium sulfate and the mixture was evaporated to produce a white solid. The yield of the product was 89%, and the NMR data were: 1H NMR (600 MHz, DMSO-d6) 5.48 (s, 2H), 3.30 (s, 9H).

Example 6

1.03 g of Compound A and 1.94 g of Compound B were added to a round-bottom flask, and it was placed in a constant-temperature oil bath at 85° C. for reaction of 0.5 h; 20 mL of propanol was added as a solvent into the round-bottom flask, and then the reaction was continued for 18 h; after the reaction was completed, the solvent was dried via a rotary drying method under reduced pressure at 70° C. to produce a white solid, which was washed several times with tetrahydrofuran, and dried in a vacuum oven to obtain Intermediate I (quaternary ammonium amine) in a bottle for use. The yield of the intermediate was 91%, and the NMR data were: 1H NMR (600 MHz, D$_2$O) 3.52 (t, 2H), 3.30 (s, 6H), 3.22 (m, 2H), 1.71 (m, 2H) 1.26-1.32 (m, 10H) 0.82 (s, 3H), 0.78 (t, 3H).

1.83 g of Intermediate I (quaternary ammonium alcohol) and 2.6 g of N, N-diisopropylethylamine was dissolved in 20 mL of dichloromethane, and the solution was added into the dropping funnel; 2.0 g of cyanuric chloride (CC) was weighed and dissolved in 30 mL of dichloromethane in a round-bottom flask, and the resultant was stirred at room temperature for 15 min; the solution in the dropping funnel dropped into the round-bottom flask, and the dropping speed was 2 h; after the addition, the reaction was carried out for 1 h, and the TLC monitored the reaction; after the reaction was completed, the solvent was removed under reduced pressure in vacuo, and petroleum ether was used to wash the mixture to produce a product. The yield of the product was 83% and the nuclear magnetic resonance data were: 1H NMR (600 MHz, Chloroform-d) 3.58 (t, 2H), 3.30 (s, 6H), 3.22 (m, 2H), 1.71 (m, 2H) 1.26-1.32 (m, 10H) 0.95 (s, 3H), 0.78 (t, 3H).

Example 7

1.26 g of Compound A and 2.78 g of Compound B were added to a round-bottom flask, and it was placed in a 35° C. constant-temperature oil bath for reaction of 8 hours; 20 mL of propanol was weighed and added as a solvent into the round-bottom flask, and then the reaction was continued for 18 h; after the reaction was completed, the solvent was dried via a rotary drying method under reduced pressure at 40° C. to produce a white solid, which was washed several times with tetrahydrofuran and dried in a vacuum oven to obtain Intermediate I (quaternary ammonium amine) in a bottle for use. The yield of the intermediate was 91%, and the NMR data were: 1H NMR (600 MHz, D$_2$O) 3.52 (t, 2H), 3.30 (s, 6H), 3.22 (m, 2H), 1.71 (m, 2H) 1.26-1.32 (m, 10H) 0.82 (s, 3H), 0.78 (t, 3H).

4.03 g of Intermediate I (amino quaternary ammonium salt) and 2.6 g of N, N-diisopropylethylamine were dissolved in 20 mL of dichloromethane, and the solution was added to the dropping funnel; 2.0 g of cyanuric chloride (CC) was dissolved in 30 mL of dichloromethane in a round-bottom flask and the mixture was stirred at room temperature for 15 min; the solution in the dropping funnel dropped into the round-bottom flask, and the dropping speed was 2 h; and after the addition, the reaction was carried out for 1 h, and the TLC monitored the reaction; after the reaction was completed, the solvent was removed under reduced pressure in vacuo, and petroleum ether was used to wash the resultant solid to produce a product. The yield of the product was 83% and the nuclear magnetic resonance data were: 1H NMR (600 MHz, Chloroform-d) 8.92 (s, 1H), 7.92 (d, 1H), 7.75 (d, 1H), 7.01 (s, N—H, 1H), 5.01 (t, 2H), 4.04 (t, 2H), 3.35 (t, 2H), 2.55 (m, 2H), 2.39 (s, 3H), 2.01 (m, 2H), 1.26-1.29 (m, 22H), 0.88 (t, 3H).

Example 8

1.23 g of Compound A and 2.20 g of Compound B were added to a round-bottom flask, and it was placed in a constant temperature oil bath at 80° C. for reaction of 1 h; 20 mL of isopropanol was added as a solvent to the round-bottom flask, and then the reaction was continued for 18 h; after the reaction was completed, the solvent was dried via a rotary drying method under reduced pressure at 40° C. to produce a white solid, and the white solid was washed several times with tetrahydrofuran and dried in a vacuum oven to obtain Intermediate I (quaternary ammonium alcohol) and it was stored in a bottle for use. The yield of the intermediate was 93%, and the NMR data were: 1H NMR (600 MHz, D$_2$O) 3.52 (t, 2H), 3.30 (s, 6H), 3.22 (m, 2H), 2.39 (s, 3H), 1.71 (m, 2H) 1.26-1.32 (m, 10H) 0.92 (s, 3H), 0.88 (t, 3H).

3.43 g of Intermediate I (quaternary ammonium alcohol) and 2.6 g N, N-diisopropyl-ethylamine was dissolved in 20 mL of dichloromethane, and the solution was added to the dropping funnel; 2.0 g of Compound C was weighed and dissolved in 30 mL of dichloromethane in a round-bottom flask and the mixture was stirred at room temperature for 15 min; the solution in the dropping funnel dropped into the round-bottom flask at the dropping speed of 1 h, and after the addition, the reaction was carried out for 30 min while monitored by TLC; after the reaction is finished, the solvent was removed under reduced pressure in vacuo, and the petroleum ether was used to wash the resultant product several times to obtain the product. The yield of the product was 88%. The NMR data were: 1H NMR (600 MHz, Chloroform-d) 8.90 (d, 2H), 7.67 (d, 2H), 5.01 (t, 2H), 3.63 (t, 2H), 2.87 (t, 2H), 2.01 (m, 2H), 1.26-1.29 (m, 14H), 0.88 (t, 3H).

Example 9

1.09 g of Compound A and 1.42 g of Compound B were added to a round-bottom flask, and it was placed in a constant temperature oil bath at 80° C. for reaction of 1 h;

20 mL of isopropanol was added as a solvent to the round-bottom flask, and then the reaction was continued for 18 h; after the reaction was completed, the solvent was dried via a rotary drying method under reduced pressure at 40° C. to produce a white solid, which was washed several times with tetrahydrofuran and dried in a vacuum oven to obtain Intermediate I (quaternary ammonium amine) in a bottle for use. The yield of the Intermediate I was 93%, and the NMR data are: 1H NMR (600 MHz, $D_2O$) 3.52 (t, 2H), 3.30 (s, 6H), 3.22 (m, 2H), 2.39 (s, 3H), 1.71 (m, 2H) 1.26-1.32 (m, 10H) 0.92 (s, 3H), 0.88 (t, 3H).

2.51 g of Intermediate I (quaternary ammonium amine) and 2.6 g of N, N-diisopropylethylamine were dissolved in 20 mL of dichloromethane, and the solution was added to the dropping funnel; 2.0 g of Compound C was weighed and dissolved in 30 mL of dichloromethane in a round-bottom flask and the mixture was stirred in an ice bath for 15 min; the solution in the dropping funnel dropped into the round-bottom flask at the dropping speed of 1 h, and after the addition, the reaction was carried out for 30 min while monitored by TLC; after the reaction was completed, the solvent was removed under reduced pressure in vacuo, and the petroleum ether was used to wash the resultant product several times. The yield of the product was 88%, and the NMR data were: 1H NMR (600 MHz, Chloroform-d) 8.95 (d, 2H), 8.61 (s, 1H), 7.80 (d, 2H), 4.38 (s, 3H), 4.31 (s, 2H).

Example 10

1.12 g of Compound A and 1.94 g of Compound B were added to a round-bottom flask, and it was placed in a 70° C. oil bath for reaction of 1 h; 20 mL of isopropanol was add as a solvent to the round-bottom flask, and then the reaction was continued for 18 h; after the reaction was over, the solvent was removed via a rotary drying method under reduced pressure at 40° C. to produce a white solid, which was washed several times with THF and dried in a vacuum oven to obtain Intermediate I (quaternary ammonium amine) and it was stored in a bottle for use. The yield of the Intermediate I was 93%.

3.06 g of Intermediate I and 0.8 g of sodium carbonate were dissolved in 10 mL of deionized water to prepare a solution to be added to the dropping funnel for use; 1.2 g (4.9 mmol) of cyanuric chloride (i.e., Compound D) was dissolved in 30 mL of tetrahydrofuran, and the mixture was added to the round-bottom flask and stirred at 40° C. for 5 min; the solution in the dropping funnel dropped into the round-bottom flask at the dropping speed of 30 min. After the addition, the reaction was continued for 30 min while monitored by TLC; after the completion of the reaction, the mixture was extracted with methylene chloride. The organic phase was dried using anhydrous sodium sulfate and the solvent of the organic phase was evaporated to produce a white solid. The yield of this product was 89% and the NMR data were: 1H NMR (600 MHz, Chloroform-d) 8.92 (s, 1H), 7.92 (s, 1H), 5.01 (m, 2H), 2.98 (d, 2H), 2.81 (d, 2H), 2.01 (m, 2H), 1.26-1.29 (m, 10H), 0.88 (t, 3H).

Example 11

1.12 g of Compound A and 333.39 g of Compound B were added into a round-bottom flask, and it was placed in a constant temperature oil bath at 75° C. for reaction of 1 h; 30 mL of dichloromethane and propanol (1:3) were added as a solvent into the round-bottom flask, and then the reaction was continued for 24 h; after the reaction was completed, the solvent was dried via a rotary drying method under reduced pressure at 60° C. to produce a white solid, which was washed several times with tetrahydrofuran, and the mixture was dried in a vacuum oven to obtain Intermediate I (quaternary ammonium alcohol) and Intermediate I was stored in a bottle for use. The yield of the intermediate was 87%, and the NMR data were: 1H NMR (600 MHz, $D_2O$) 8.92 (s, 1H), 7.92 (d, 4H), 4.80 (m, 2H), 4.37 (m, 5H), 3.63 (t, 2H), 1.26-1.95 (m, 32), 0.97 (d, 2H).

4.45 g of Intermediate I (quaternary ammonium alcohol) and 2.6 g of N, N-diisopropylethylamine were dissolved in 20 mL of dichloromethane, and the solution was added into the dropping funnel; 2.0 g of cyanuric chloride (CC) was dissolved in 30 mL of dichloromethane in a round-bottom flask and the mixture was stirred at room temperature for 15 min; the solution in the dropping funnel dropped into the round-bottom flask, and the dropping speed was 2 h, and after the addition, the reaction was carried out for 1 h, and the TLC monitored the reaction; after the reaction was completed, the solvent was removed under reduced pressure in vacuo, and petroleum ether was used to wash the resultant solid to produce a product. The yield of the product was 83% and the nuclear magnetic resonance data were: 1H NMR (600 MHz, Chloroform-d) 8.92 (s, 1H), 7.92 (d, 4H), 4.80 (m, 2H), 4.37 (m, 5H), 3.72 (t, 2H), 1.26-1.95 (m, 32), 0.97 (d, 2H).

Example 12

1.12 g of Compound A and 0.95 g of Compound B were added to the round-bottom flask, and it was placed in a constant temperature oil bath at 65° C. for reaction of 1 h; 20 mL of dichloromethane was added as a solvent to the round-bottom flask, and then the reaction was continued for 18 h; after the reaction was completed, the solvent was dried via a rotary drying method under reduced pressure at 40° C. to produce a white solid, which was washed several times with tetrahydrofuran and dried in a vacuum oven to obtain Intermediate I (quaternary ammonium alcohol) and stored in a bottle for use. The yield of the intermediate was 91%, and the NMR data were: 1H NMR (600 MHz, $D_2O$) 8.92 (s, 1H), 7.92 (d, 4H), 4.33-4.37 (m, 5H), 3.63 (t, 2H).

2.08 g of Intermediate I (quaternary ammonium alcohol) and N, N-diisopropyl-ethylamine 2.6 g was dissolved in 20 mL of dichloromethane, and it was added to the dropping funnel; 2.0 g of cyanuric chloride (CC) was dissolved in 30 mL of dichloromethane in a round-bottom flask and the mixture was stirred at room temperature for 15 min; the solution in the dropping funnel dropped into the round-bottom flask, and the dropping speed was 2 h, and after the addition, the reaction was carried out for 1 h, and the TLC monitored the reaction; after the reaction was completed, the solvent was removed under reduced pressure in vacuo, and petroleum ether was used to wash the resultant solid to produce a product. The yield of the product was 83% and the nuclear magnetic resonance data were: 1H NMR (600 MHz, Chloroform-d) 8.92 (s, 1H), 7.92 (d, 4H), 7.75 (d, 1H), 4.58 (t, 2H), 4.49 (t, 2H), 4.36 (s, 3H), 2.39 (s, 3H).

Example 13

3.36 g of Compound A and 0.95 g of Compound B were added to a round-bottom flask, and it was placed in a constant temperature oil bath at 65° C. for reaction of 1 h; 20 mL of isopropanol were added as a solvent to the round-bottom flask, and then the reaction was continued for 24 h; after the reaction was completed, the solvent was dried via a rotary drying method under reduced pressure at 60° C.

to produce a white solid, which was washed several times with tetrahydrofuran, and dried in a vacuum oven to obtain Intermediate I (quaternary ammonium alcohol) and stored in a bottle for use. The yield of the intermediate was 91%, and the NMR data are: 1H NMR (600 MHz, $D_2O$) 8.92 (s, 1H), 7.92 (d, 4H), 4.33-4.37 (m, 5H), 3.63 (t, 2H), 1.26-1.95 (m, 32).

4.32 g of Intermediate I (quaternary ammonium alcohol) and 2.6 g of N, N-diisopropyl-ethylamine was dissolved in 20 mL of dichloromethane, and the solution was added into the dropping funnel; 2.0 g of cyanuric chloride (CC) dissolved in 30 mL of dichloromethane in a round-bottom flask and the mixture was stirred at room temperature for 15 min; the solution in the dropping funnel dropped into the round-bottom flask, and the dropping speed was 2 h, and after the addition, the reaction was carried out for 1 h, and the TLC monitored the reaction; after the reaction was completed, the solvent was removed under reduced pressure in vacuo, and petroleum ether was used to wash the resultant solid to produce a product. The yield of the product was 83%, and the nuclear magnetic resonance data were: 1H NMR (600 MHz, Chloroform-d) 8.92 (s, 1H), 7.92 (d, 4H), 4.33-4.37 (m, 5H), 3.75 (t, 2H), 1.26-1.95 (m, 32).

Example 14

1.26 g of Compound A and 0.95 g of Compound B were added to the round-bottom flask, and it was placed for reaction at 65° C. for 2 h; 20 mL of propanol was added as a solvent into the round-bottom flask, and then the reaction was continued for reaction of 18 h; after the reaction was completed, the solvent was dried via a rotary drying method under reduced pressure at 40° C. to produce a white solid, which was washed several times with tetrahydrofuran and dried in a vacuum oven to obtain Intermediate I (quaternary ammonium amine) in a bottle for use. The yield of the intermediate was 91%, and the NMR data were: 1H NMR (600 MHz, $D_2O$) 8.92 (s, 2H), 7.75 (s, 6H), 4.36 (s, 2H).

2.21 g of Intermediate I (quaternary ammonium alcohol) and 2.6 g of N, N-diisopropyl-ethylamine were dissolved in 20 mL of dichloromethane, and the solution was added into the dropping funnel; 2.0 g of cyanuric chloride (CC) was dissolved in 30 mL of dichloromethane in a round-bottom flask and the solution was stirred at room temperature for 15 min; the solution in the dropping funnel dropped into the round-bottom flask, and the dropping speed was 2 h, and after the addition, the reaction was carried out for 1 h, and the TLC monitored the reaction; after the reaction was completed, the solvent was removed under reduced pressure in vacuo, and petroleum ether was used to wash the resultant solid to produce a product. The yield of the product was 83% and the nuclear magnetic resonance data were: 1H NMR (600 MHz, Chloroform-d) 8.98 (s, 1H), 7.92 (d, 1H) 7.76 (d, 1H), 4.36 (s, 3H), 4.04 (t, 2H), 2.68 (t, 2H), 2.58 (m, 2H).

Example 15

1.09 g of Compound A and 0.95 g of Compound B were added to a round-bottom flask, and it was placed in a constant temperature oil bath at 80° C. for 1 h; 20 mL of ethanol was added as a solvent to the round-bottom flask, and then the reaction was continued for reaction of 18 h; after the reaction was completed, the solvent was dried via a rotary drying method under reduced pressure at 40° C. to produce a white solid, which was washed several times with tetrahydrofuran and dried in a vacuum oven to obtain Intermediate I (quaternary ammonium alcohol) and the Intermediate I was stored in a bottle for use. The yield of the intermediate was 93%, and the NMR data were: 1H NMR (600 MHz, $D_2O$) 9.01 (d, 2H), 8.22 (d, 2H), 4.61 (s, 2H), 4.38 (s, 3H).

2.04 g of Intermediate I (quaternary ammonium alcohol) and 2.6 g of N, N-diisopropyl-ethylamine were dissolved in 20 mL of dichloromethane, and the solution was added to the dropping funnel; 2.0 g of cyanuric chloride (CC) was dissolved in 30 mL of dichloromethane in a round-bottom flask and the solution was stirred at room temperature for 15 min; the solution in the dropping funnel dropped into the round-bottom flask, and the dropping speed was 1 h, and after the addition, the reaction was carried out for 30 min while monitored by TLC; after the end of the reaction, the solvent was removed under reduced pressure in vacuo, and the petroleum ether was used to wash the resultant solid several times to produce the product. The yield of the product was 88%. The NMR data were: 1H NMR (600 MHz, Chloroform-d) 9.01 (d, 2H), 8.22 (d, 2H), 4.83 (s, 2H), 4.38 (s, 3H).

Example 16

1.40 g of Compound A and 4.52 g of Compound B were added to a round-bottom flask, and it was placed in a constant temperature oil bath at 65° C. for reaction of 1 h; 20 mL of isopropanol was added as a solvent to the round-bottom flask, and then the reaction was continued for 24 h; after the reaction was completed, the solvent was dried via a rotary drying method under reduced pressure at 60° C. to produce a white solid, which was washed several times with tetrahydrofuran, and dried in a vacuum oven to obtain Intermediate I (quaternary ammonium alcohol) and the Intermediate I was stored in a bottle for use. The yield of the intermediate was 91%, and the NMR data were: 1H NMR (600 MHz, $D_2O$) 9.01 (d, 2H), 8.22 (d, 2H), 4.81 (d, 2H), 4.61 (d, 2H), 4.38 (s, 3H), 1.26-1.95 (m, 32).

6.38 g of Intermediate I (quaternary ammonium alcohol) and 2.6 g of N, N-diisopropylethylamine was dissolved in 20 mL of dichloromethane, and the solution was added into the dropping funnel; 2.0 g of cyanuric chloride (CC) was dissolved in 30 mL of dichloromethane in a round-bottom flask and the solution was stirred at room temperature for 15 min; the solution in the dropping funnel dropped into the round-bottom flask, and the dropping speed was 2 h, and after the addition, the reaction was carried out for 1 h, and the TLC monitored the reaction; after the reaction was completed, the solvent was removed under reduced pressure in vacuo, and petroleum ether was used to wash the resultant solid to produce a product. The yield of the product was 83% and the nuclear magnetic resonance data were: 1H NMR (600 MHz, Chloroform-d) 4.01 (t, 4H), 2.60 (t, 2H), 2.26 (t, 2H), 1.26-1.30 (m, 40H), 0.88 (s, 6H).

The preparation process of the product (i.e., the antimicrobial and anti-mite compound) according to Examples 17 to 19 below was carried out in three steps, and the reaction route was as follows:

A+B→Intermediate I

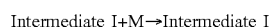

Intermediate I+M→Intermediate I

Intermediate II+D→E

The structural formulas of the compounds A, B, Intermediate I, M, Intermediate II, D and E in Examples 17 to 19 are shown in Table 3, respectively.

TABLE 3

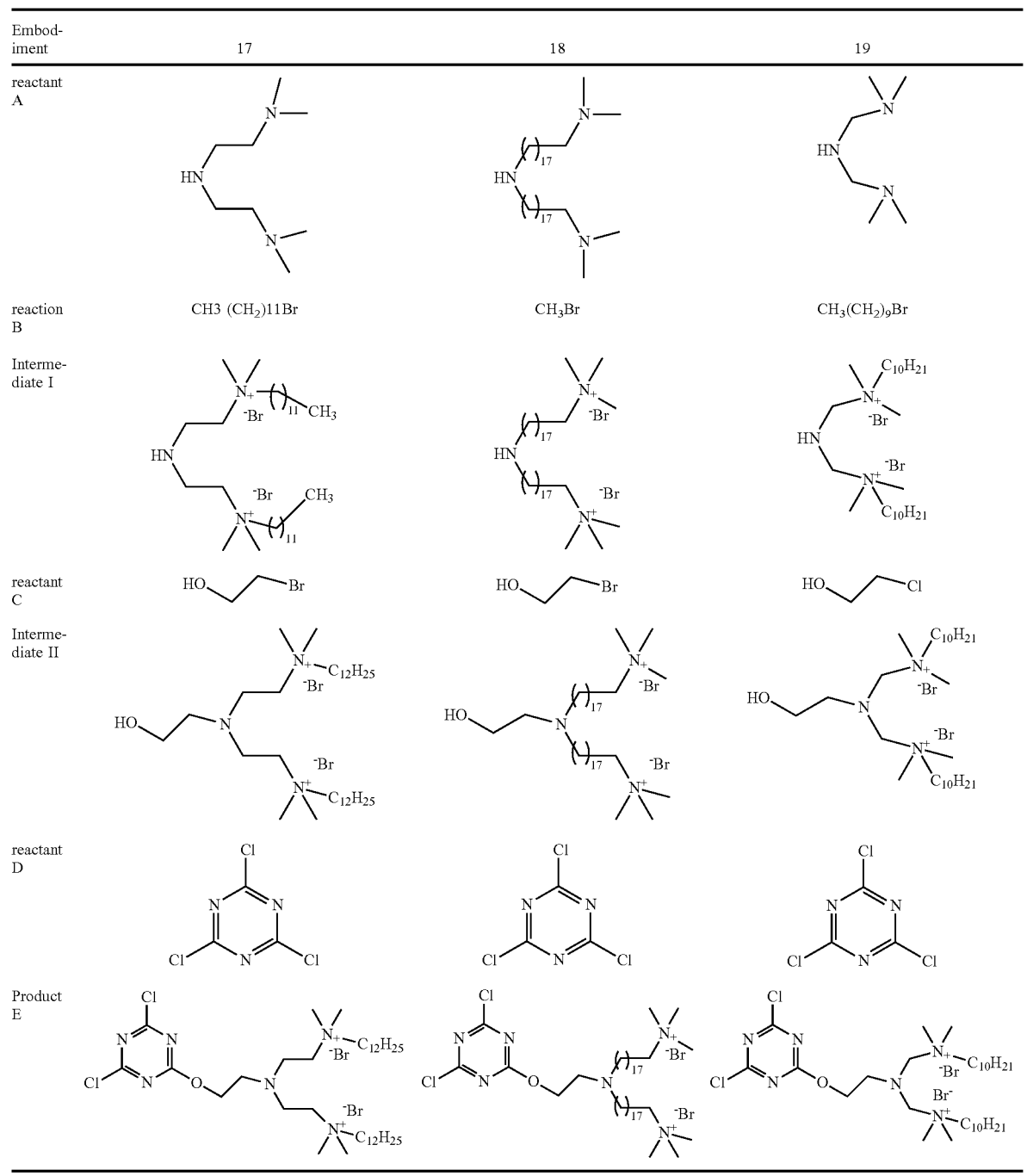

The reaction conditions of each embodiment are as follows.

Example 17

1.69 g of Compound A and 2.2 g of Compound B were added into a 250 mL round-bottom flask, the mixture was stirred at room temperature for reaction of 2 h; 50 mL of acetone was added to the round-bottom flask and the mixture was stirred for reaction of 12 h at this temperature to obtain Intermediate I. Then, 1.37 g of Compound C and 1.3 g of N,N-diisopropyl-ethylamine were added into the round-bottom flask under stirring and the reaction was continued for 12 h under the protection of ultrapure nitrogen to obtain a hydroxyl group-containing biquaternary ammonium salt (Intermediate II), and the solution was added into the dropping funnel. 1.85 g of Compound D was dissolved in 100 mL of tetrahydrofuran and the solution was added to the round-bottom flask, stirring at 0° C. for 5 min; the solution in the dropping funnel was dropped into a round-bottom flask, and the dripping speed was controlled for 30 min. After the addition, the reaction was continued for 30 min while monitored by TLC; after the reaction was completed, it was spin-dried to obtain a white solid, and acetone was washed and purified several times to obtain a product. The yield of this product was 78%. The nuclear magnetic resonance data of the product was 1H NMR (600 MHz, Chloroform-d): 3.42 (t, 2H), 3.34 (t, 4H), 3.30 (s, 12H), 3.22 (t, 4H), 2.80 (t, 4H), 2.57 (t, 2H), 1.71 (m, 4H), 1.26-1.29 (m, 36H), 0.88 (t, 6H).

Example 18

6.08 g of Compound A and 1.88 g of Compound B were added into a 250 mL round-bottom flask, and the mixture was stirred at room temperature for reaction of 2 h; 100 mL of acetone was added to the round-bottom flask under stirring for 12 h at this temperature to obtain Intermediate I. Then, 1.37 g of Compound C and N, N-diisopropyl-ethylamine 1.3 g were added to the round-bottom flask under stirring and the reaction was continued for 12 h under the protection of ultrapure nitrogen to obtain a hydroxyl group-containing biquaternary ammonium salt (Intermediate II), and the solution was added into the dropping funnel. 1.85 g of Compound D was dissolved in 100 mL of tetrahydrofuran and the mixture was added to the round-bottom flask and stirred at 0° C. for 5 min; the solution in the dropping funnel dropped into the round-bottom flask, and the dripping speed was controlled for 30 min. After the addition, the reaction was continued for 30 min while monitored by TLC; after the reaction was completed, it was spin-dried to obtain a white solid, and acetone was washed and purified several times to obtain a product. The yield of this product was 85%. The nuclear magnetic resonance data of the product was 1H NMR (600 MHz, Chloroform-d): 3.42 (t, 2H), 3.30 (s, 18H), 3.22 (t, 4H), 2.46 (t, 4H), 2.57 (t, 2H), 1.71 (m, 4H), 1.29-136 (m, 60H).

Example 19

1.31 g of Compound A and 4.42 g of Compound B were added into a 250 mL round-bottom flask and stirred at room temperature for reaction of 2 h; 50 mL of acetone was added, and the stirring was continued at this temperature for 12 h to obtain Intermediate I. Then, 0.88 g of Compound C and 1.3 g N, N-diisopropyl-ethylamine were added into the round-bottom flask and the mixture was stirred for continuing the reaction for 12 h under the protection of ultrapure nitrogen to obtain a hydroxyl group-containing biquaternary ammonium salt (Intermediate II), and the solution was added into the dropping funnel. 1.85 g of Compound D dissolved in 100 mL of tetrahydrofuran, and the solution was added to the round-bottom flask and stirred at 0° C. for 5 min; the solution in the dropping funnel was dropped into the round-bottom flask at the dropping speed of 30 min. After the addition, the reaction was continued for 30 min while monitored by TLC; after the reaction was completed, the mixture was spin-dried to obtain a white solid, and acetone was used several times to wash and purify the product. The yield of this product was 80%. The nuclear magnetic resonance data of the product was 1H NMR (600 MHz, Chloroform-d): 4.31 (s, 4H), 3.42 (t, 2H), 3.30 (s, 12H), 3.22 (t, 4H), 2.53 (t, 2H), 1.71 (m, 4H), 1.26-1.29 (m, 28H), 0.88 (t, 6H).

The preparation process of the product (i.e., the antimicrobial and anti-mite compound) according to Examples 20 to 21 below was carried out in two steps, and the reaction route was as follows:

A+B→Intermediate I

Intermediate I+D→E

The structural formulas of the compounds A, B, Intermediate I, D and E in embodiments 20 to 21 are shown in Table 4.

TABLE 4

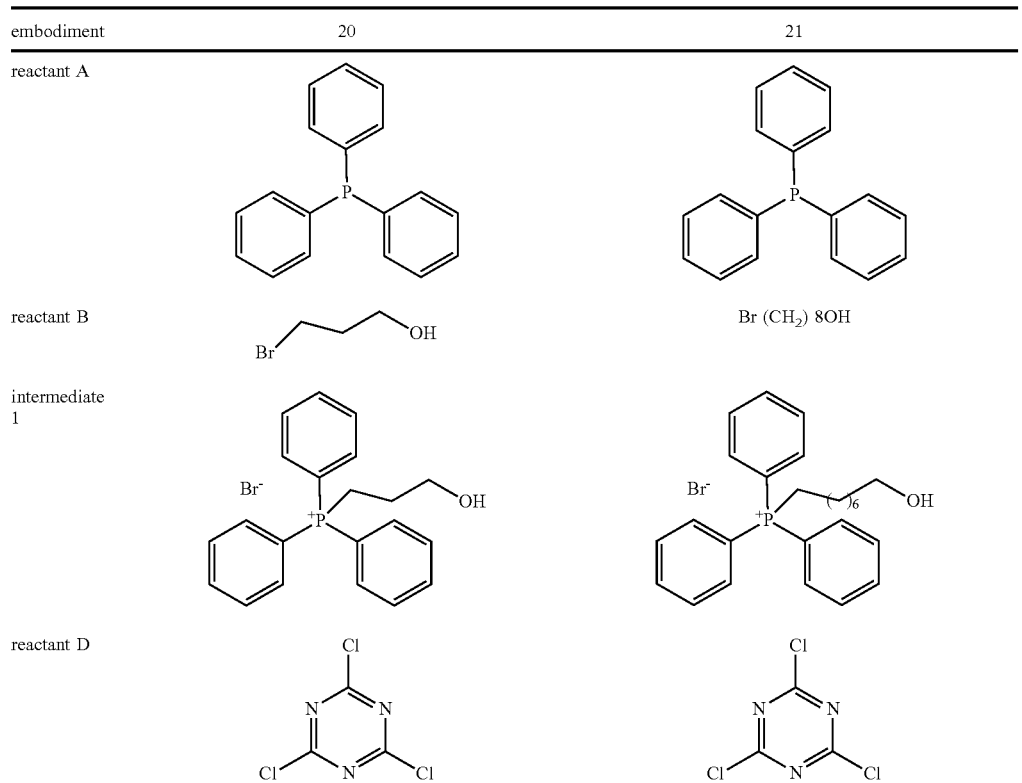

TABLE 4-continued

| embodiment | 20 | 21 |
|---|---|---|
| product E | (structure shown) | (structure shown) |

The reaction conditions of each embodiment are as follows.

Example 20

2.62 g of Compound A was dissolved in 20 mL of toluene and transferred to 100 mL of a three-neck round bottom flask. 1.5 g of Compound B was added to the three-neck round bottom flask, and the reaction was conducted under high purity nitrogen gas at 50° C. with constant stirring for reaction of 36 h. The reaction mixture was washed repeatedly with petroleum ether to produce Intermediate I.

4.02 g of the intermediate product I and 2.6 g of N, N-diisopropyl-ethylamine were dissolved in 30 mL of tetrahydrofuran, and the solution was added into the dropping funnel. Then, 1.85 g of Compound D (dissolved in 20 mL of tetrahydrofuran) was added to the round-bottom flask, and the solution was stirred at 0° C. for 5 min; the solution in the dropping funnel dropped into the round-bottom flask, and the dripping speed was 30 min. After the addition, the reaction was continued for 30 min. TLC monitored the reaction; after the reaction was over, the organic phase was extracted with anhydrous sodium sulfate and dried to produce a white solid, that is, compound E. The total yield of the product was 55%. The nuclear magnetic resonance data of this product is: 1H NMR (600 MHz, Chloroform-d) 1.5 (m, 2H), 2.46 (t, 2H), 3.49 (t, 2H), 7.33-7.36 (m, 15H).

Example 21

2.62 g of Compound A was dissolved in 20 mL of toluene and transferred to 100 mL of a three-neck round bottom flask. 2.4 g of Compound B was added into the three-neck round bottom flask for reaction of 36 h under high purity nitrogen and 50° C. with constant stirring, and the resultant mixture was washed repeatedly with petroleum ether to produce Intermediate I.

6.22 g of intermediate product I and 2.6 g of N, N-diisopropyl-ethylamine were dissolved in 30 mL of tetrahydrofuran, and the solution was add to the dropping funnel. Then, 1.85 g of Compound D (dissolved in 20 mL of tetrahydrofuran) was added to the round-bottom flask, and the solution was stirred at 0° C. for 5 min; the solution in the dropping funnel dropped into the round-bottom flask at the dripping speed of 30 min. After the addition, the reaction was continued for 30 min. TLC monitored the reaction; after the reaction was over. The organic phase was extracted with anhydrous sodium sulfate and dried to produce a white solid. That is, compound E, the total yield of the product was 52%. The nuclear magnetic resonance data of this product is: 1H NMR (600 MHz, Chloroform-d) 1.22-1.39 (m, 10H), 1.49 (m, 2H), 2.43 (t, 2H), 3.45 (t, 3H), 7.33-7.36 (m, 15H).

Example 22—Anti-Microbial Effects of Compound E

Each of the reaction products (i.e., compound E) according to Examples 1-21 was used to prepare an anti-microbial agent (e.g., a finishing liquid), and the anti-microbial effects were different depending on compound E and conditions of use.

The anti-microbial effects of compound E obtained in Examples 1 to 21 were compared, as shown in Table 5 below.

TABLE 5

| | Anti-microbial rate (%) of cotton textiles finished with compound E (1.0 wt %) | | | | | | | | |
|---|---|---|---|---|---|---|---|---|---|
| | Escherichia Coli (E. coli, ATCC25922) | | | Staphylococcus Aureus (S. aureus, ATCC 6538) | | | Candida Albicans (C. albicans 10231) | | |
| Times of washing | 0 | 10 | 50 | 0 | 10 | 50 | 0 | 10 | 50 |
| Comparative Experiment | 99.9 | 83 | 75 | 99.9 | 86 | 80 | 95 | 78 | 69 |
| Example 1 | 99.99 | 99.9 | 99.2 | 99.99 | 99.9 | 99.8 | 99.9 | 99.9 | 98.9 |
| Example 2 | 99.99 | 99.9 | 99.9 | 99.99 | 99.9 | 99.9 | 99.9 | 99.9 | 98.5 |
| Example 3 | 99.99 | 99.9 | 99.2 | 99.99 | 99.9 | 99.9 | 99.9 | 99.9 | 99.9 |
| Example 4 | 99.99 | 99.9 | 99.9 | 99.99 | 99.9 | 99.9 | 99.9 | 99.9 | 99.9 |
| Example 5 | 99.99 | 99.9 | 99.1 | 99.99 | 99.9 | 99.9 | 99.9 | 99.9 | 97.9 |
| Example 6 | 99.99 | 99.9 | 99.5 | 99.99 | 99.9 | 99.9 | 99.9 | 99.9 | 97.9 |
| Example 7 | 99.99 | 99.9 | 99.9 | 99.99 | 99.9 | 99.9 | 99.9 | 99.9 | 98.6 |
| Example 8 | 99.99 | 99.9 | 99.5 | 99.99 | 99.9 | 99.9 | 99.9 | 99.9 | 98.9 |

TABLE 5-continued

| | Anti-microbial rate (%) of cotton textiles finished with compound E (1.0 wt %) | | | | | | | | |
|---|---|---|---|---|---|---|---|---|---|
| | Escherichia Coli (E. coli, ATCC25922) | | | Staphylococcus Aureus (S. aureus, ATCC 6538) | | | Candida Albicans (C. albicans 10231) | | |
| Times of washing | 0 | 10 | 50 | 0 | 10 | 50 | 0 | 10 | 50 |
| Example 9 | 99.99 | 99.9 | 99.9 | 99.99 | 99.9 | 99.9 | 99.9 | 99.9 | 99.2 |
| Example 10 | 99.99 | 99.9 | 99.6 | 99.99 | 99.9 | 99.9 | 99.9 | 99.9 | 98.7 |
| Example 11 | 99.99 | 99.9 | 99.9 | 99.99 | 99.9 | 99.9 | 99.9 | 99.9 | 99.6 |
| Example 12 | 99.99 | 99.9 | 98.9 | 99.99 | 99.9 | 99.5 | 99.9 | 99.9 | 91.9 |
| Example 13 | 99.99 | 99.9 | 99.5 | 99.99 | 99.9 | 99.9 | 99.9 | 99.9 | 98.9 |
| Example 14 | 99.99 | 99.9 | 99.1 | 99.99 | 99.9 | 99.5 | 99.9 | 99.9 | 99.9 |
| Example 15 | 99.99 | 99.9 | 98.9 | 99.99 | 99.9 | 99.1 | 99.9 | 99.9 | 92.9 |
| Example 16 | 99.99 | 99.9 | 99.8 | 99.99 | 99.9 | 99.9 | 99.9 | 99.9 | 93.6 |
| Example 17 | 99.99 | 99.9 | 99.5 | 99.99 | 99.9 | 99.9 | 99.9 | 99.9 | 99.3 |
| Example 18 | 99.99 | 99.9 | 97.9 | 99.99 | 99.9 | 98.9 | 99.9 | 99.9 | 96.9 |
| Example 19 | 99.99 | 99.9 | 99.7 | 99.99 | 99.9 | 98.8 | 99.9 | 99.9 | 97.9 |
| Example 20 | 99.99 | 99.9 | 95.9 | 99.99 | 99.9 | 97.9 | 99.9 | 99.9 | 92.9 |
| Example 21 | 99.99 | 99.9 | 96.9 | 99.99 | 99.9 | 98.9 | 99.9 | 99.9 | 93.9 |

Remarks: 1) in the data of anti-microbial rate in Table 5: Examples 1-9 used a soaking-rolling-drying process to finish cotton fabric, where the bath ratio (i.e., the ratio of the weight of a liquid containing compound E to the weight of the cotton fabric) was 20:1, the residual liquid ratio was 90%, and the drying process was conducted at 85° C. for 30 minutes; Examples 10-18 were prepared by a soaking-high speed spinning-drying method, where the bath ratio was 20:1, the residual liquid ratio was 90%, and the drying process was conducted at 85° C. for 20 min; Examples 19-21 were prepared by a spraying-spinning-drying process with a bath ratio of 30:1, a residual liquid ratio of 85% after drying, and the drying process was conducted at 105° C. for 5 minutes.

2) Table 5 data test method: FZ/T73023-2006 anti-microbial textiles D.8 shocking method. In addition, the inhibition zone method (FZ/T73023-2006 anti-microbial textiles—Appendix E—inhibition zone method) was used to test whether the active compound (E) was released from the finished cotton textiles, the inhibition zone test result of the 21 examples and zwitterions were 0 mm, and thus compound E was not released from the finished cotton textiles. The anti-microbial finishing agent used in the comparative experiment was zwitterion with the molecular structure

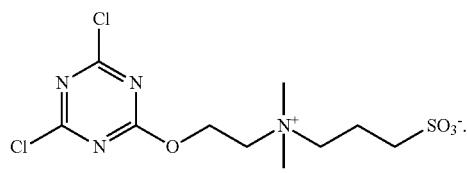

The finishing process and concentration of the test using zwitterion were consistent with those of Examples 1-9.

3) The composition of the finishing liquid in Table 5 was: compound E 1.0 wt %, sodium bicarbonate 1.0 wt %, and the rest of the finishing liquid was water.

In addition, the present disclosure provides other examples of anti-microbial results as follows.

(1) A comparison of the anti-microbial effects of textiles soaked with compound E obtained in Example 2 and unsoaked textiles was shown in FIG. 1. The experimental procedure was: The anti-microbial performance of the finishing text was tested by the shock method (GB/T 20944.3-2007). The tested microorganism were Gram-negative Escherichia coli (E. coli, ATCC 25922) and Gram-positive Staphylococcus Aureus (S. Aureus, ATCC 6538). The specific experimental operations are as follows: 1) inoculating and culturing the microorganisms at 37° C. for 14 h; diluting the microbial solution to $10^{-5}$ using a sterilized PBS buffer (pH=7.2) to obtain a diluted microbial solution; 2) taking the same size of blank textiles (e.g., cloth) and textiles (finished using compound E and sterilized) in different 50 mL tubes, adding 5 mL of diluted microbial solution to immerse the textiles, sealing the tubes and putting the tubes on a shaker for shaking the tubes under 37° C. at 190 r/min for 24 h; 3) after 24 hours of cultivation, the tubes were taken out and diluted to 10 times using a PBS solution. 100 μL of the diluted microbial solution was added to the nutrient agar medium, uniformly spread to dryness, placed in an incubator, and cultured at 37° C. for 16 h, and then the plates were taken out, and the number of colonies in each plate was counted. The anti-microbial rate was calculated by the following equation:

Anti-microbial rate (%)=[($N_1$−$N_0$)/$N_0$]×100%.

Notes: $N_1$ denotes the number of colonies in the finished cloth; $N_0$ denotes the number of colonies in blank cloth.

The inhibition zone method was used to test the dissolution (or release) of compound E in the finished cloth.

The results showed that the anti-microbial rates of E. coli and S. aureus were more than 99.5%, 99.9%, and that compound E in the anti-microbial textiles was not released.

Figure 2:
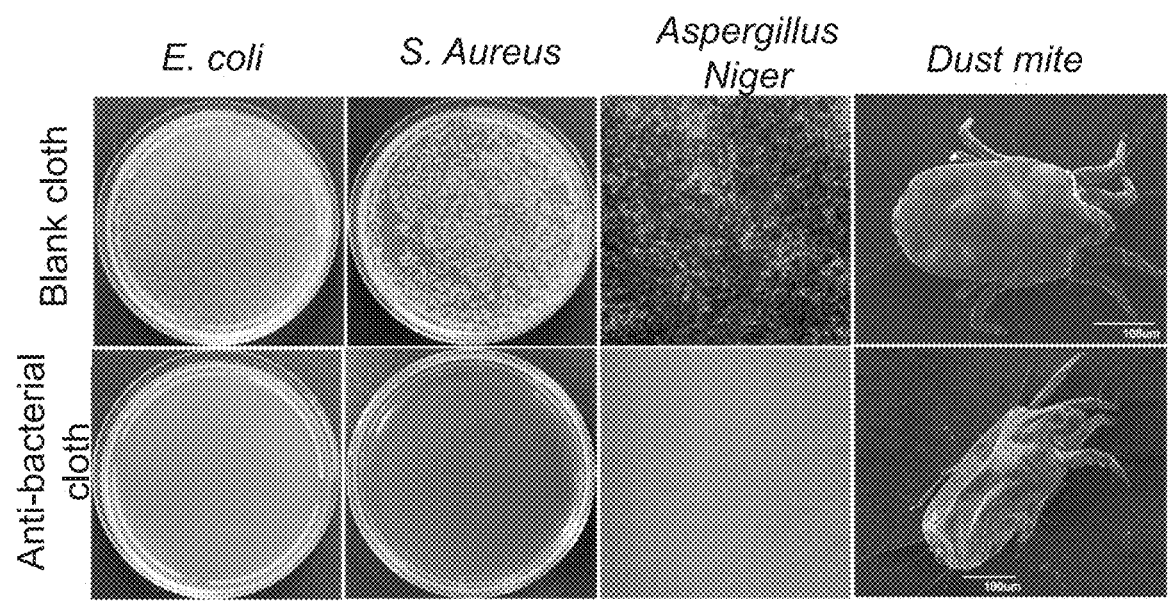
FIG. 2 is a group of images showing anti-microbial, anti-mildew effects of textiles treated with compound E obtained in Example 11 (1.0 wt %) according to some embodiments of the present disclosure.

(2) A comparison of the anti-microbial effects of textiles soaked with compound E obtained in Example 11 and unsoaked textiles was shown in FIG. 2. The experimental procedure was as follows: the anti-microbial performance of the finished textiles was tested by the live cell counting method, and the anti-mite activity of the house dust mites was evaluated according to the national standard method (GB/T 24253-2009). The results showed that the bacteriostatic rate of Gram-negative bacteria (E. coli), Gram-positive bacteria (Staphylococcus aureus) and fungi (Aspergillus niger) was over 99.99%, and it had good acaricidal activity against house dust mites.

Figure 3:
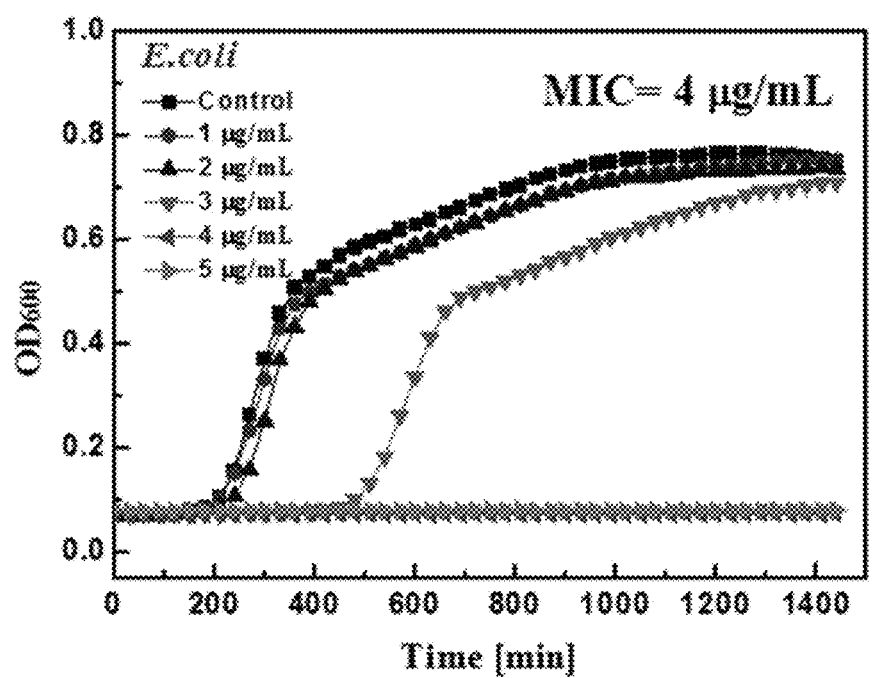
FIG. 3 is an analytical graph showing anti-*E. coli* effects at different concentrations of compound E obtained in Example 19 according to some embodiments of the present disclosure.
Figure 4:
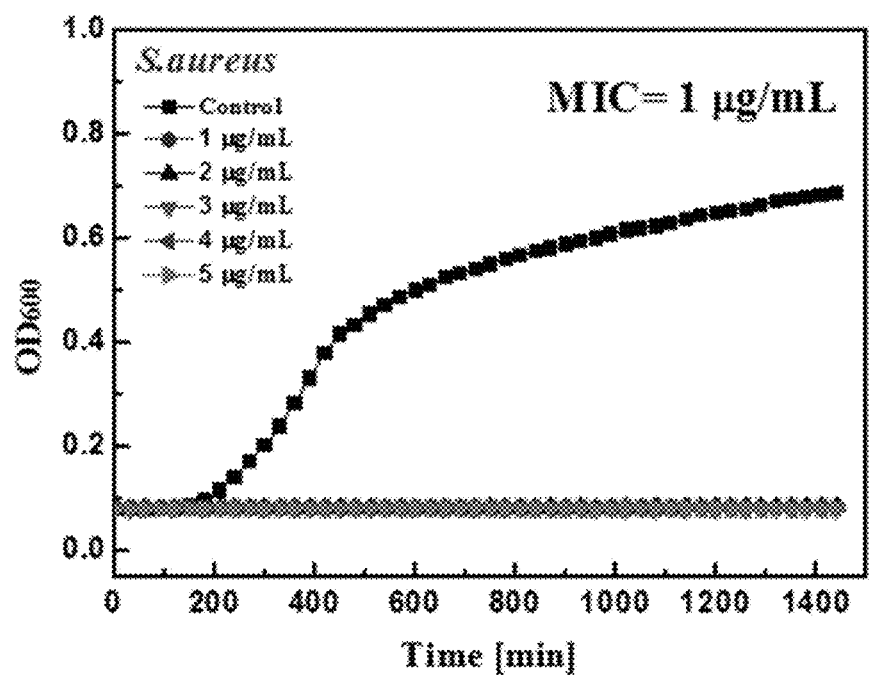
FIG. 4 is an analytical graph showing anti-*S. aureus* effects at different concentrations of compound E obtained in Example 19 according to some embodiments of the present disclosure.
Figure 5:
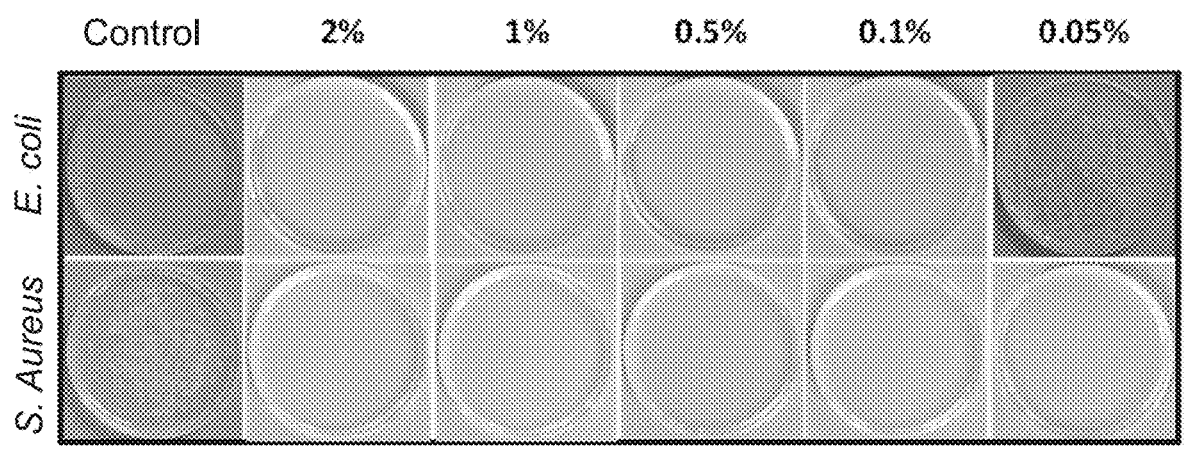
FIG. 5 is a group of images showing anti-microbial effects of cloth finished by compound E obtained in Example 19 at different concentrations according to some embodiments of the present disclosure.

Example 23—the Anti-Microbial Effects of Textiles Finished with Compound E at Various Concentrations The inhibitory effect of compound E obtained in Example 19 on Escherichia coli and Staphylococcus Aureus at various concentrations was shown in FIGS. 3 to 5. The experimental procedure was: using the enzyme linked immunosorbent assay to determine the minimal inhibitory concentration (MIC) value of the anti-microbial drug, and adding the diluted anti-microbial drug solution to the sterilized 100-well plate, respectively. Specifically, 10 ul of drug solution (i.e., a solution of compound E) was added to the first to eleventh holes at concentrations of 100 μg/ml, 90 μg/ml, 80 μg/ml, 70 μg/ml, 60 μg/ml, 50 μg/ml, 40 μg/ml, 30 μg/ml, 20 μg/ml, 10 μg/ml, 5 μg/ml. The drug solution was not added to the twelfth hole which serves as a control group; the bacterial suspension was diluted by LB broth (0.5 Mcfarland Standard dilution to 1000 times with a bacterial concentration of 105 colony-forming unit (CFU)/ml), and 90 μl of the bacterial suspension was added to each well. At this time, the drug concentrations of the first to the eleventh holes were 10 μg/ml, 9 μg/ml, 8 μg/ml, 7 μg/ml, and 6 μg/ml, 5 μg/ml, 4 μg/ml, 3 μg/ml, 2 μg/ml, 1 μg/ml, 0.5 μg/ml respectively. The change curve of $OD_{600}$ value for 24 h was measured in a microplate reader (automatic growth-curve machine). 2.0 wt %, 1.0 wt %, 0.5 wt %, 0.1 wt %, 0.05 wt % anti-microbial finishing liquid was prepared and used to finish textiles (cloth) according to the finishing process, respectively, and the anti-microbial performance of the finished cloth was tested by the shock method (GB/T 20944.3-2007). The results showed that the minimum inhibitory concentration against *Escherichia coli* was 4 μg/ml, and the minimum inhibitory concentration against *Staphylococcus Aureus* was 1 μg/ml. The anti-microbial rate of the anti-microbial finishing liquid having a concentration of compound E that is >0.1% against *S. aureus* and *E. coli* was >99.9%.

Figure 6:
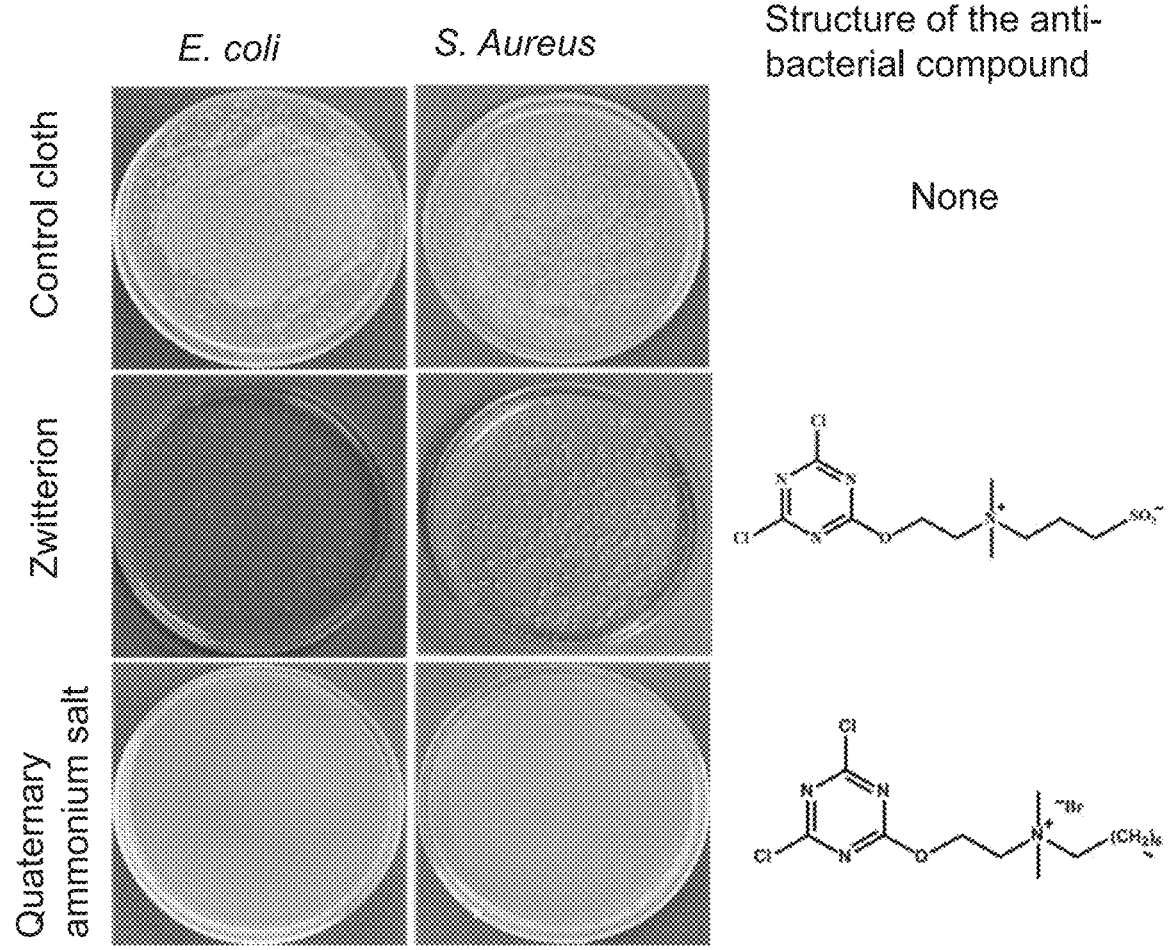
FIG. 6 is a group of images showing anti-microbial effects of cloth finished by compound E obtained in Example 1 and zwitterion according to some embodiments of the present disclosure.

Example 24—the Anti-Microbial Effects of Textiles Finished by Quaternary Ammonium Salt are Better than Those of Textiles Finished by Zwitterion Solution at the Same Concentration The inhibitory effect of compound E in Example 1 and zwitterion on *E. coli* and *S. aureus* was compared, and the results are shown in FIG. 6. The experimental procedure was as follows: a finishing liquid containing the quaternary ammonium salt (Example 1) and a zwitterionic anti-microbial finishing liquid with the same concentration of 1.0 wt % were subjected to anti-microbial finishing of textiles, and the anti-microbial performance of the finished textiles was tested by the shock method (GB/T 20944.3-2007). The results showed that at the same concentration, the anti-microbial activity of the quaternary ammonium finishing liquid on *S. aureus* and *E. coli* was greater than that of the zwitterionic finishing liquid.

Example 25—Compound E was Grafted onto the Surface of the Textiles

Figure 7:
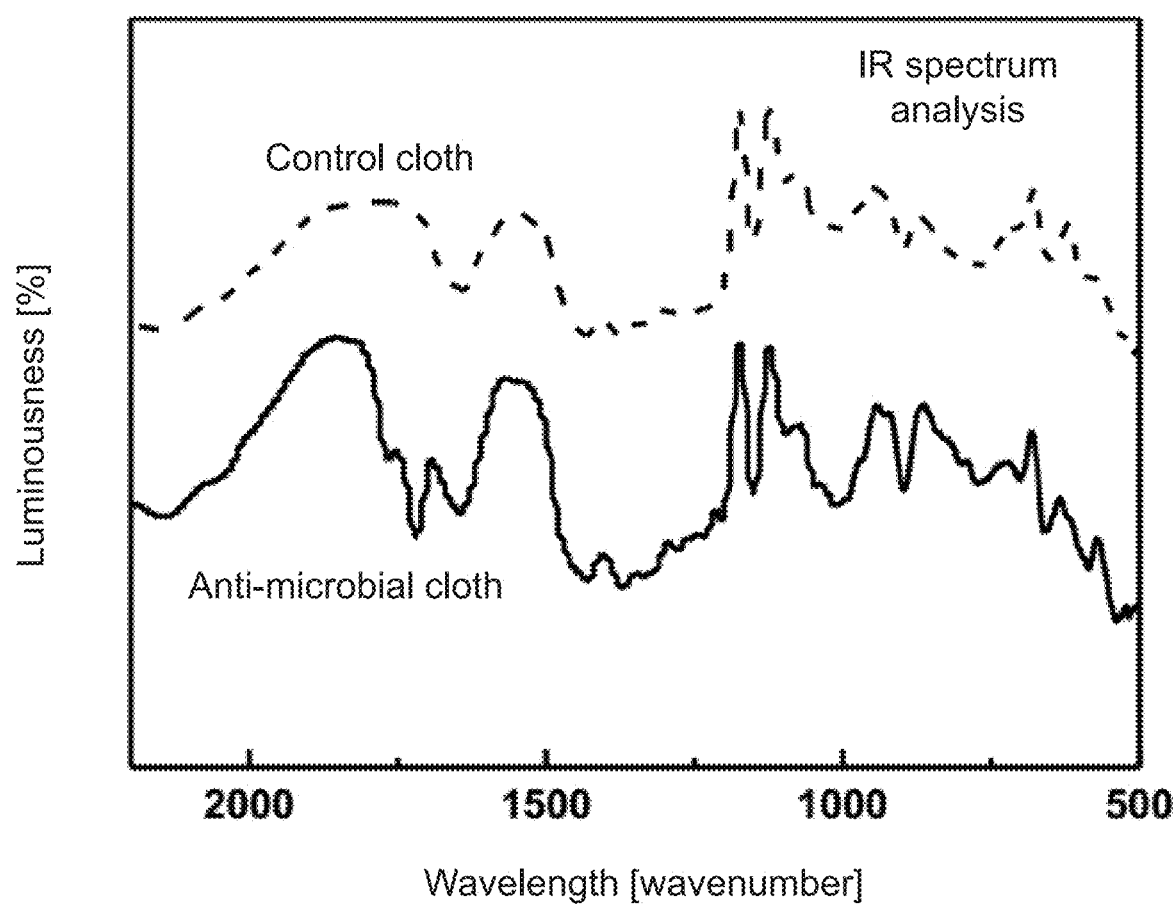
FIG. 7 is an analysis graph showing an infrared spectrum analysis result of anti-microbial cloth finished by compound E obtained in Example 1 according to some embodiments of the present disclosure.

The infrared (IR) spectrum analysis result of cloth finished by compound E obtained in Example 1 (the concentration of compound E in the finishing liquid was 1.0 wt %) was shown in FIG. 7. The experimental process is: using the infrared spectral reflectance (ATR) technique to compare the structure of the textiles, before and after finishing, at a scanning range of 400~4000 $cm^{-1}$ and the resolution of 4 $cm^{-1}$ for 32 scans and. The results showed that the triazine ring and the quaternary ammonium group existed in the textiles finished by compound E compared to the unfinished textiles, indicating that compound E was grafted on the surface of the textiles.

Figure 8:
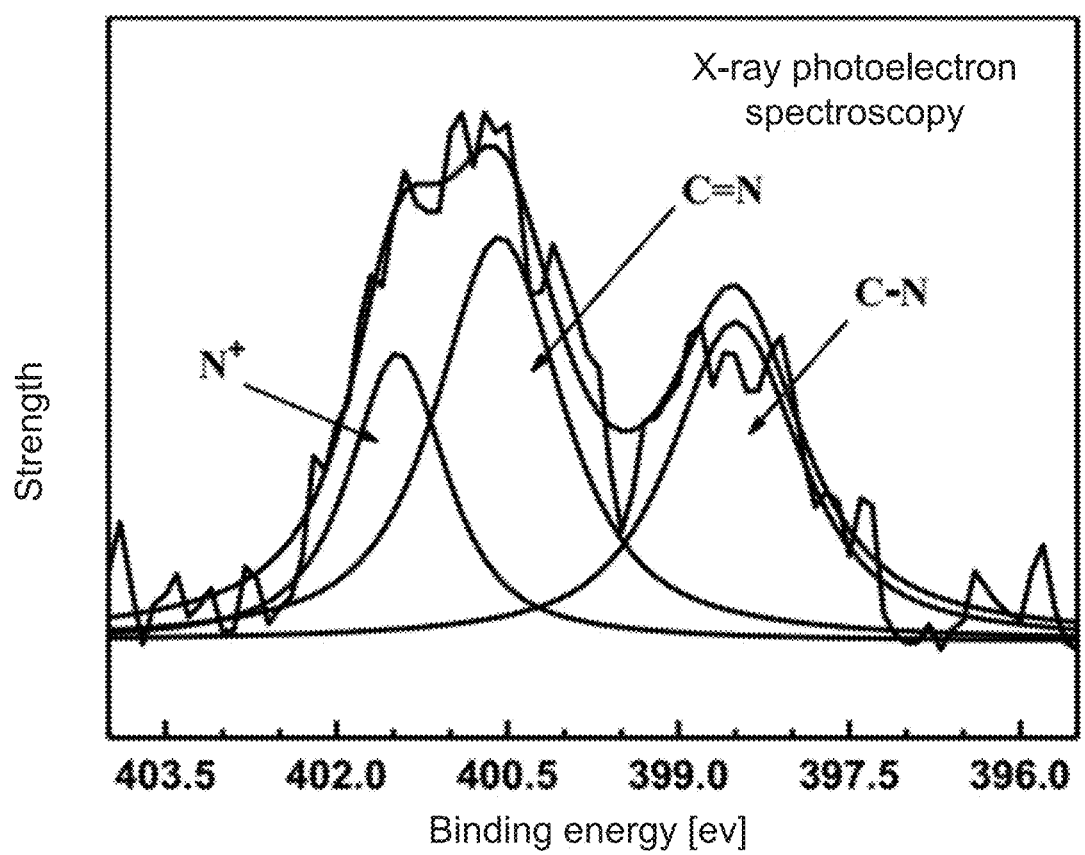
FIG. 8 is an analysis graph showing a result of X-ray photoelectron spectroscopy analysis of anti-microbial cloth finished by compound E obtained in Example 1 according to some embodiments of the present disclosure.

The X-ray photoelectron spectroscopy analysis result of the textiles finished by compound E obtained in Example 1 (the concentration of compound E in the finishing liquid was 1.0 wt %) was as shown in FIG. 8. The experimental procedure was: X-ray photoelectron spectroscopy (XPS, ULVAC-PHI 1800) was used to analyze the elemental composition of the finished textiles and unfinished textiles, and the chemical valence of the nitrogen (N) element was determined. The Al target (1486.6 ev) was used as the radiation source, and the test elevation angle was 75°.

The results showed that the textiles finished by compound E had more N signal peaks in the scanning spectrum. The N1s may fit into three peaks with a combined energy of 398.5 ev, 399.9 ev, and 402 ev, respectively related to C=N, C—N, $N^+$. These three types of peaks coincided with the type of N on compound E, indicating that compound E was grafted on the textiles surface in a chemically bonded manner.

It should be noted that the composition of the ROVIDIUM is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

We claim:

1. A compound, having a structure represented by a general formula (I):

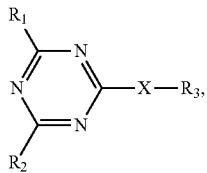

wherein $R_1$ is halogen;
$R_2$ is H, halogen, —$NO_2$ or $C_{1-8}$ hydrocarbyl that is unsubstituted or substituted with one or more heteroatoms;
X is O or S; and
$R_3$ is

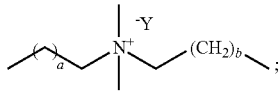

wherein:
a=0-17;
b=0-17; and
Y is halogen.

2. A method of preparing the compound (I) of claim 1, comprising:
reacting HX—$R_3$ with a compound having a structure represented by the general formula (III) to obtain the compound (I).

3. The method of claim 2, wherein the reacting HX—$R_3$ with a compound having a structure represented by the general formula (III) to obtain the compound (I) includes:
reacting HX—$R_3$ with the compound having the structure represented by the general formula (III) under the presence of a Lewis base, wherein the Lewis base is preferably selected from the group consisting of alkali metal, inorganic base of alkaline earth metal, and an organic tertiary amine.

4. The method of claim 3, wherein
the inorganic base is selected from the group consisting of sodium hydroxide, potassium hydroxide, magnesium hydroxide, calcium hydroxide, potassium carbonate, potassium hydrogencarbonate, sodium carbonate, sodium hydrogencarbonate, and combinations thereof; and
the organic tertiary amine is selected from the group consisting of N, N-diisopropyl-ethylamine, trimethylamine, triethylamine, N, N-dimethyl-n-octylamine, N, N-dimethylaniline, N, N-dimethyl-dodecylamine, N, N-dimethyl-dodecylamine, N, N-dimethyl-hexadecylamine, N, N-dimethyl-octadecylamine, N, N-dimethyl-decylamine, dimethylaminoethyl methacrylate, diethylaminoethyl methacrylate, and combinations thereof.

5. An anti-microbial or anti-mite product, comprising the compound of claim 1.

6. The product of claim 5, wherein the content of the compound is 0.05%-10% of the product by weight.

7. The product of claim 5, wherein the content of the compound is 0.1-5% of the product by weight.

8. The product of claim 5, wherein the pH of the product is between 8-11.

9. The product of claim 5, wherein the product is used to kill microorganisms or mites, the microorganisms including at least one of *Escherichia Coli, Staphylococcus Aureus, Candida Albicans*, or *Aspergillus Niger*.

10. The product of claim 5, wherein the product is a finishing agent for treating textiles, fibers, or yarns.

* * * * *